(12) United States Patent
Bensimon et al.

(10) Patent No.: US 7,368,234 B2
(45) Date of Patent: May 6, 2008

(54) PHYSICAL MAPPING METHOD USING MOLECULAR COMBING TECHNIQUE ALLOWING POSITIONING OF A GREAT NUMBER OF CLONES WITHIN A GENOME

(75) Inventors: Aaron Bensimon, Antony (FR); David Bensimon, Paris (FR); Xavier Michalet, Paris (FR)

(73) Assignee: Institut Pasteur, Paris (FR)

( * ) Notice: Subject to any disclaimer, the term of this patent is extended or adjusted under 35 U.S.C. 154(b) by 271 days.

(21) Appl. No.: 10/386,354

(22) Filed: Mar. 11, 2003

(65) Prior Publication Data

US 2004/0033510 A1 Feb. 19, 2004

Related U.S. Application Data

(63) Continuation of application No. 09/921,302, filed on Aug. 3, 2001, now abandoned, which is a continuation of application No. 09/297,302, filed as application No. PCT/FR97/01949 on Oct. 30, 1997, now Pat. No. 6,344,319.

(30) Foreign Application Priority Data

Oct. 30, 1996 (FR) .................................. 96 13276
Mar. 13, 1997 (FR) .................................. 97 02999

(51) Int. Cl.
*C12Q 1/68* (2006.01)
(52) U.S. Cl. ......................................................... 435/6
(58) Field of Classification Search .................... 435/6; 436/94
See application file for complete search history.

(56) References Cited

U.S. PATENT DOCUMENTS

| | | | |
|---|---|---|---|
| 5,079,169 A | 1/1992 | Chu et al. | |
| 5,356,776 A | 10/1994 | Kambara et al. | |
| 5,660,988 A | 8/1997 | Duck et al. | |
| 5,677,126 A | 10/1997 | Bensimon et al. | |
| 5,707,797 A | 1/1998 | Windle | |
| 5,840,862 A | 11/1998 | Bensimon et al. | |
| 5,846,724 A | 12/1998 | Bensimon et al. | |
| 5,851,769 A | 12/1998 | Gray et al. | |
| 6,054,327 A | 4/2000 | Bensimon et al. | |
| 6,265,153 B1 | 7/2001 | Bensimon et al. | |
| 6,294,324 B1 | 9/2001 | Bensimon et al. | |
| 6,303,296 B1 | 10/2001 | Bensimon et al. | |
| 6,548,255 B2 | 4/2003 | Bensimon et al. | |
| 2003/0175779 A1 | 9/2003 | Bensimon et al. | |

FOREIGN PATENT DOCUMENTS

| | | | |
|---|---|---|---|
| WO | WO 93/18186 | 9/1993 | |
| WO | WO 95/09929 | 4/1995 | |
| WO | WO 95/21939 | 8/1995 | |
| WO | WO 96/17958 | 6/1996 | |
| WO | WO 97/18326 | 5/1997 | |

OTHER PUBLICATIONS

Parra et al., Nature Genetics 5, 17-21 (1993).*
Lebofsky et al., Briefings in Functional Genomics and Proteomics 1(4), 385-396 (2003).*
Lichter et al., "High-Resolution Mapping of Human Chromosomes 11 by In Situ Hybridization With Cosmid Clones", *Science*, vol. 247, pp. 64-69 (1990).
du Manoir et al., "Detection of Complete and Partial Chromosome Gains and Losses by Comparative Genomic In Situ Hybridization", *Hum. Genet.*, vol. 90, pp. 590-610 (1993).
Kallioniemi et al., "Comparative Genomic Hybridization for Molecular Cytogenic Analysis of Solid Tumors," *Science*, vol. 258, pp. 818-821 (Oct. 30, 1992).
International Search Report for PCT/FR97/01949 (and English version), Oct. 30, 1997.
Desmaze et al., "In Situ Hybridization of Fluorescent Probes on Chromosomes, Nuclei or Stretched DNA: Applications in Physical mapping and Characterization of Genomic Rearrangements", *Cellular and Molecular Biology*, 41(7), pp. 925-931 (1995).
du Manoir et al., "Quantitative Analysis of Comparative Genomic Hybridization", *Cytometry*, vol. 19, pp. 27-41 (1995).
Bensimom et al., "Alignment and Sensitive Detection of DNA by a Moving Interface", *Science*, vol. 265, pp. 2096-2098 (Sep. 30, 1994).
Piper et al., "Computer Image Analysis of Comparative Genomic Hybridization", *Cytometry*, vol. 19, pp. 10-26 (1995).
Michalet et al., *Science*, vol. 277, pp. 1518-1523 (Sep. 1997).

* cited by examiner

*Primary Examiner*—Kenneth R. Horlick
(74) *Attorney, Agent, or Firm*—Finnegan, Henderson, Farabow, Garrett & Dunner, LLP

(57) ABSTRACT

A method for detecting or locating one or several genes of one or several specific A DNA sequence or one or several molecules reacting with DNA on a B DNA where the method can include: (a) fixing and combing a certain amount of the B DNA on a combing surface; (b) reacting the product of step (a) with one or several probes, linked with the gene(s) or specific A DNA sequences, or with the molecules capable of reacting with DNA; (c) extracting information corresponding to at least one of the following categories: (1) the position of the probes, (2) the distance between the probes, (3) the size of the probes (the total sum of sizes for quantifying the number of hybridized probes) and determining from this extracted information the presence, the location and/or the amount of a gene(s) or specific A DNA sequences. This method can be used in particular for the diagnosis of genetic diseases.

10 Claims, 22 Drawing Sheets

255A6 (SURF ctg) & 220F3 (ctg 37)

20kb

180F1 (ctg 37) & 50D9 (DBH ctg)

20kb

PHYSICAL MAPPING METHOD USING MOLECULAR COMBING TECHNIQUE ALLOWING POSITIONING OF A GREAT NUMBER OF CLONES WITHIN A GENOME

This is a continuation of application Ser. No. 09/921,302, filed Aug. 3, 2001, (abandoned), which is a continuation of Ser. No. 09/297,302, which is a 371 national stage filing, completed on Jul. 9, 1999, of International application PCT/FR97/01949, filed Oct. 30, 1997, and which issued as U.S. Pat. No. 6,344,319 on Feb. 5, 2002, all of which are incorporated herein by reference.

The present invention relates in particular to a method for detecting and locating polynucleotide sequences (which may contain or otherwise genes or gene portions) in a genome or a genome portion using the so-called molecular combing technique.

The present invention also relates to a method for detecting and locating reagents of biological, natural or synthetic origin by combining said reagents with all or part of the combed DNA.

The technique of molecular combing, as described in the following references: PCT/FR95/00164 of Oct. 2, 1995 and PCT/FR95/00165 of Oct. 2, 1995, applied to nucleic acids, and more particularly to genomic DNA, allows the uniform extension and the visualization of DNA or of RNA in the form of rectilinear and practically aligned filaments.

The present invention is based on the demonstration of the fact that, using probes, that is to say polynucleotides containing a chain of nucleotide sequences such as labeled DNA molecules which specifically recognize portions of the aligned DNA, which are hybridized with the combed DNA, it is possible to directly visualize, on the combed genome, the position of the complementary sequence.

Under these conditions, it is possible, for example using two probes labeled with different chromophores such that they can be visualized by a color, red and green for example, to measure the distance separating them. However, it is also possible, using different probes or a series of contiguous probes (called hereinafter "contig"), to directly measure the length of the region of interest, and to measure the potential impairments thereof in the case of an abnormal genome.

The present invention therefore relates, in particular, to the diagnosis of genetic diseases which are preferably characterized by substantial impairments of the genome, either in its structure, deletion or translocation for example, or in the number of copies of certain sequences (trisomy for example, where the sequence represents the whole of a chromosome), as well as to methods which allow genes to be located and mapped rapidly.

Genetic diagnosis may be divided into several fields:
prenatal,
pathologies with a genetic component,
cancer and susceptibility to cancer.

Prenatal Diagnosis

The majority (95%) of fetal abnormalities are due to trisomies of chromosomes 21, 18, 13, X or Y. Their conclusive diagnosis is somewhat late (17th week of amenorrhea, by amniocentesis for example). Aminiocentesis requires a substantial puncture of amniotic fluid (a few tenths of milliliters) from which fetal cells in suspension are extracted and cultured for several days (see the technique described by S. Mercier and J. L. Bresson (1995) Ann. Génét., 38, 151-157). A karyotype of these cells is established by macroscopic observation and counting the chromosomes by a highly specialized staff.

A technique involving the collection of chorial villi makes it possible to dispense with the culturing step and avoids the collection of amniotic fluid. Karyotype analysis requires, however, the same work (see Médecine Prénatale. Biologie Clinique du Foetus. André Boué, Publisher Flammarion, 1989). These two techniques may be applied earlier (up to 7 weeks of gestation for the collection of chorial villi and 13-14 weeks for aminiocentesis), but with a slightly increased risk of abortion. Finally, a direct collection of fetal blood at the level of the umbilical cord allows karyotyping without culturing, but presupposes a team of clinicians specialized in this technique (C. Donner et al., 1996, Fetal Diagn. Ther., 10, 192-199).

Other abnormalities such as translocations or deletions/insertions of substantial portions of chromosomes may be detected at this stage, or by using techniques such as fluorescent in situ hybridization (FISH). However, here again, this type of diagnosis can only be carried out by a highly qualified staff.

Studies show, moreover, that there are as yet no immunological methods allowing the detection of fetal markers in maternal blood allowing a conclusive diagnosis of trisomy 21 or of other abnormalities (see, for example, N. J. Wald et al., 1996, Br. J. Obstet. Gynaecol., 103, 407-412 for trisomy 21—related Down's syndrome).

The current prenatal diagnoses therefore have numerous disadvantages: they can only be carried out at a relatively late stage of the development of the embryo; they are not completely without risk for the fetus or for the mother; the results are often obtained after a fairly long time (about 1 to 3 weeks depending on the technique) and they are costly. Finally, a number of chromosomal abnormalities go undetected.

Diagnosis of Pathologies with a Genetic Component

Many diseases have a recognized genetic component (diabetes, hypertension, obesity and the like) which is the result of deletions, insertions and/or chromosomal rearrangements of variable sizes. The culturing of cells does not pose any problem at this stage, but the FISH techniques, which are described by G. D. Lichter et al.(1993), Genomics, 16, 320-324; B. Brandritt et al., (1991), Genomics, 10, 75-82 and G. Van den Hengh et al., (1992), Science, 257, 1410-1412) have a limited resolution and require a highly qualified staff, making these tests barely accessible.

The development of a more effective and inexpensive test would allow the general adoption of suitable therapies, at an early stage of the pathologies involved, likely to improve their remission.

Cancer Diagnosis

Among the pathologies with a genetic component, cancerous conditions constitute a major class affecting an increasing proportion of the population. Current understanding of the process of the onset of a cancerous condition involves a step of proliferation of proto-oncogenes (mutations in the genome of the cells) which precedes the transformation of the cell to a cancerous cell. This proliferation step is unfortunately not detectable, whereas the possibility of carrying out a treatment at this stage would certainly increase the chances of remission and would reduce the patients' handicap.

Finally, a number of tumors are characterized by chromosomal rearrangements such as translocations, deletions, partial or complete trisomies, and the like.

In each of these fields, molecular combing can provide a major contribution, either by the speed and the small quantity of biological material needed, or by the quantitative accuracy of the results.

The importance of the technique appears most particularly in the case where the genetic material is obtained from cells which are no longer dividing or which cannot be cultured, or even from dead cells in which the DNA is not significantly degraded.

In the case of prenatal diagnosis, such is the case after extraction of fetal cells circulating in the maternal blood (Cheung et al., 1996, Nature Genetics 14, 264-268). The same applies in the case of cancerous cells obtained from certain tumors.

Molecular combing makes it possible to improve the possibilities of diagnosis of genetic diseases, but it may also allow the study and identification of the genomic sequences responsible for said diseases. Moreover, currently, the development of a diagnostic "kit" or box starts with the search for the gene involved in the pathology.

The search for genes involved in pathologies (human or other) is nowadays generally carried out in several steps:

(i) Establishment of a target population of individuals effected by the pathologies, of their descendants, ascendants and collaterals, and collection of blood and/or cell samples for the purpose of storing genetic material (in the form of DNA or of cellular strains).

(ii) Genetic location by analysis of probability of cosegregation with genetic markers (linkage analysis). At this stage of the study, a few close markers located on one or more given chromosomes are available which make it possible to proceed to the step of physical location.

(iii) Physical mapping: starting with the genetic markers obtained in the preceding step, a screening of libraries of human DNA clones (YACs, BACs, cosmids and the like) specific for the region(s) determined in the preceding step is carried out. A number of clones containing the preceding markers are thus obtained. The region of interest may then be precisely mapped using clones of decreasing size. Cloning of the genome portion considered may also be carried out again using the human DNA.

(iv) Search for the gene: several techniques may be used at this stage: exon "trapping" (use of cDNA libraries (complementary DNAs obtained from messenger RNA)) CpG islands, preservation of interspecific sequences, and the like, which make it possible to assign a coding sequence to one (or more) of the clones selected in the preceding steps.

This strategy as a whole represents a major work (up to several years possibly). Consequently, any technique which makes it possible to arrive more quickly at step (iv) constitutes an advantage for, the search for genes, but also in diagnosis.

In the current state of the art, when the gene has been located, for example by the preceding method, its detection is in general carried out using specific probes corresponding to the sequence in question, the latter being amplified by methods of the PCR type for example or the LCR type (as described in patent EP 0 439 182) or a technique of the NASBA type (kit marketed by the company Organon Teknika).

However, amplification techniques are not completely satisfactory, especially for heterozygotes, since a normal copy of the gene exists in the genome, as well as in the case of a large deletion or of diseases involving repetitive sequences where PCR is not satisfactory either.

The diagnosis of a large number of genetic diseases can now be envisaged using molecular combing and labeling of DNA.

Molecular combing is a technique which consists in anchoring DNA molecules by their ends to surfaces under well defined physicochemical conditions, followed by their stretching with the aid of a receding meniscus; DNA molecules aligned in a parallel manner are thus obtained. The purified DNA used may be of any size, and therefore in particular genomic DNA extracted from human cells. The genome may also be obtained from a genomic material containing at least 80% genetic material of fetal origin.

The DNA molecules thus combed may be denatured before being hybridized with nucleic acid probes labeled by any appropriate means, (in particular with biotin-dUTP or digoxygenin-dUTP nucleotides), which are then revealed, for example, with the aid of fluorescent antibody systems.

Given that molecular combing is characterized by a constant extension of the combed molecules, the measurement of the lengths of the fluorescent fragments observed with the aid of an epifluorescence microscope (for example) therefore directly gives the size of the hybridized probe fragments.

The degree of extension depends on the type of surface, but can be precisely measured; it is for example 2 kilobases (kb) per micrometer (μm) in the case of surfaces silanized according to the protocol described in reference (1) and used in the examples.

When necessary, it is possible to provide for an internal standard, that is to say a so-called calibrating DNA of known length which will make it possible to calibrate the operation, that is to say to calibrate each measurement.

The present invention, which includes various embodiments, relates essentially to a method for detecting the presence or the location of one or more genes or of one or more sequences of specific A DNA or of one or more molecules reacting with the DNA on a B DNA, characterized in that:

(a) a certain quantity of said B DNA is attached to and combed on a combing surface,
(b) the B combing product is reacted with one or more labeled probes, bound to the gene(s) or to the sequences of specific A DNA(s) or to the molecules capable of reacting with the DNA,
(c) the information corresponding to at least one of the following categories is extracted:
  (1) the position of the probes,
  (2) the distance between probes,
  (3) the size of the probes (the total sum of the sizes which make it possible to quantify the number of hybridized probes)
    so as to deduce therefrom the presence, the location and/or the quantity of the genes or of the sequences of specific A DNA.

In the present description, the combing technology refers to the technology described in the documents mentioned above, likewise the notion of "combing surface" which corresponds to a treated surface allowing anchorage of the DNA and its stretching by a receding meniscus.

It should be noted that the combing surface is preferably a flat surface on which readings are easier.

"Reaction between the labeled probes and the combed DNA" is understood to mean any chemical or biochemical reaction, in particular immunological type reactions (for example antibody directed against methylated DNA), protein/DNA or nucleic acid/DNA (for example hybridization between complementary segments) or nucleic acid/RNA, or nucleic acid/RNA-DNA hybrid reactions. There may also be mentioned, as examples, DNA-DNA chemical binding reactions using molecules of psoralen or reactions for polymerization of DNA with the aid of a polymerase enzyme.

The hybridization is generally preceded by denaturation of the attached and combed DNA; this technique is known and will not be described in detail.

"Probe" is understood to designate both a mono- or double-stranded polynucleotide, containing at least 20 synthetic nucleotides or a genomic DNA fragment, and a "contig", that is to say a set of probes which are contiguous or which overlap and covers the region in question, or several separate probes, labeled or otherwise. "Probe" is also understood to mean any molecule bound covalently or otherwise to at least one of the preceding entities, or any natural or synthetic biological molecule which may react with the DNA, the meaning given to the term "reaction" having been specified above, or any molecule bound covalently or otherwise to any molecule which may react with the DNA.

In general, the probes may be identified by any appropriate method; they may be in particular labeled probes or alternatively nonlabeled probes whose presence will be detected by appropriate means. Thus, in the case where the probes were labeled with methylated cytosines, they could be revealed, after reaction with the product of the combing, by fluorescent antibodies directed against these methylated cytosines. The elements ensuring the labeling may be radioactive but will preferably be cold labelings, by fluorescence for example. They may also be nucleotide probes in which some atoms are replaced.

The size of the probes may be understood to be of any value measured with an extensive unit, that is to say such that the size of two probes is equal to the sum of the sizes of the probes taken separately. An example is given by the length, but a fluorescence intensity may for example be used. The length of the probes used is between for example 5 kb and 40-50 kb, but it may also consist of the entire combed genome.

Advantageously, in the method in accordance with the invention, at least one of the probes is a product of therapeutic interest which is capable of interacting with the DNA. Preferably, the reaction of the probe with the combed DNA is modulated by one or more molecules, solvents or other relevant parameters.

Finally, in general, "genome" will be used in the text which follows; it should be clearly understood that this is a simplification; any DNA or nucleic acid sequence capable of being attached to a combing surface is included in this terminology.

In addition, the term "gene" will sometimes be used indiscriminately to designate a "gene portion" of genomic origin or alternatively a specific synthetic "polynucleotide sequence".

In a first embodiment, the method according to the invention is used to allow the screening of breaks in a genome, as well as for the positional cloning of such breaks. It should be noted that the term "break" covers a large number of local modifications of the genome of which the list will be explicitly stated later.

The method according to the present invention consists in determining the position of the potential break points involved in a pathology of genetic origin by hybridization, to combed genomic DNA of patients suffering from said pathology, of a genomic probe of known size (cloned or otherwise) situated in the region of the desired gene. These break points consist of points in the genetic sequence whose surroundings change over several kilobases (kb) between a healthy individual and a diseased individual.

The principle of the definition of the break point is based on the possibility of detecting, by molecular combing, a local modification of the genome studied compared with a genome which has already been studied, at the level of the region(s) considered.

The development of methods for picking out local modifications of the genome of less than 1 kb in size can thus be envisaged with the aid of close-field observation techniques (AFM, STM, SNOM, and the like) or techniques having an intrinsically higher resolution (for example gold nanobead electron microscopy).

More particularly, the present invention relates to a method for identifying a genetic abnormality of a break in a genome, characterized in that:
(a) a certain quantity of said genome is attached to and combed on a combing surface,
(b) the combing product is hybridized with one or more labeled specific probes corresponding to the genomic sequence for which the abnormality is sought,
(c) the size of the fragments corresponding to the hybridization signals and optionally their repetition are measured, and
(d) the presence of a break is deduced therefrom either by direct measurement or by comparison with a standard corresponding to a control length.

By way of illustration, the measurement of the size of the fragments leads to a histogram, that is to say a graphical representation of the lengths of the fragments observed.

In order to produce a histogram of the probe, the number of clones having a defined probe length is evaluated. In principle, the histogram contains only one or two peaks depending on the type of break analyzed, two peaks when the probe hybridizes as two separate fragments and a single peak when it hybridizes as a single fragment.

In the case of a heterozygous genome, in which one of the alleles is normal for the region considered, the signature of the normal allele (the absence of a break) is superposed on that of the abnormal allele, but can be extracted because of the fact that it is known.

This method can also be used to carry out positional cloning, that is to say to determine the position of one or more unknown genes involved in a pathology. The principle consists, as before, in hybridizing clones of human or animal or plant DNA, serving in this case as probe, to the combed genomic DNA of one or more patients suffering from the pathology studied. The revealing of these hybridizations makes it possible to measure the size of the hybridized fragments and to construct a histogram of the various sizes observed. If the clone used as probe covers a break point of the gene, the signature of this phenomenon will be legible on the length (shorter) of the hybridized fragment.

The use of a limited number of clones specific for the implicated region which may have been deduced by genetic linkage analysis will thus allow a rapid and precise determination of the position of a break point, of a deletion or of any other genetic rearrangement of sufficient size to be resolved by the detection technique combined with the molecular combing.

Obviously in this case, the break is searched out in order to map it; in the diagnosis, the break is known; it is its presence or its absence which is searched out.

Two possibilities may exist (on the assumption that a break point exists in the region of the genome involved in the pathology):

(i) the probe does not overlap the break point, (ii) the probe overlaps the break point.

In case (i), the measurement of the lengths of the fluorescent probes is comparable to that which would be obtained with the same probe hybridized to a nonpathogenic genomic DNA of the same nature (that is to say essentially of the same size and prepared under the same conditions).

In case (ii), on the other hand, the probe being systematically hybridized to two separate pieces (or more) in the combed genomic DNA (by definition of the existence of a break point), the measurement of the lengths of the hybridized fluorescent probes is different from the result obtained by hybridization to a non pathological genomic DNA. Moreover, the size of the fragments hybridized to the pathogenic DNA makes it possible to estimate the position of the break point in the clone with a precision of a few kb, or even more, if a more resolutive technique is used.

Because of this, only the search for the gene in this clone now therefore remains. Basically, it will involve repeating these measurements for all the clones which are likely to partially cover the region corresponding to the gene. The number of hybridization slides may be reduced by simultaneously hybridizing several differently labeled probes, or by using a method of coding by combination of colors, as will be described below.

This technique makes it possible to determine the position of the potential break points of the region, of the genome, involved in a genetic pathology by hybridization of cloned genomic DNA to combed genomic DNA obtained from patients. This technique therefore applies to the search for regions of the genome which are responsible for pathologies due to:

the deletion of a portion or of the whole of this region of the genome, the translocation of all or part of this region of the genome, the duplication or presence of several copies of all or part of this region of the genome inside it or at any other site of the genome, the insertion of any genetic sequence inside this region of the genome.

In a second embodiment and in some specific cases, in particular when the genetic abnormality searched out contains major deletions or duplications (in the case of trisomies for example), the method which is the subject of the present invention may be modified since it then involves assaying the genes or a particular sequence.

More particularly, the present invention relates to a method for assaying a given genomic sequence in a genome, characterized in that:

(a) a certain quantity of said genome is attached to and combed on a combing surface, (b) the combing product is hybridized with a labeled control probe of length lt corresponding to a so-called control genomic sequence, that is to say whose copy number in the genome is known, and with a labeled specific probe of length lc corresponding to the genomic sequence to be assayed, such that said probes may be identified separately, (c) the total length of the hybridization signals for the two probes, that is to say Lc and Lt, is then measured, (d) the copy number of the corresponding sequence is calculated for each by the ratio $$Nt = \frac{Lt}{lt} \text{ and } Nc = \frac{Lc}{lc}$$

and the copy number of the sequence to be assayed relative to the control sequence is deduced therefrom.

In the case of the prenatal diagnosis of trisomy 21, the method may consist in the hybridization of a cosmid probe specific for a control chromosome (chromosome 1, for example probe of length lt), labeled with biotinylated nucleotides, and the hybridization of a cosmid probe specific for chromosome 21 (probe of length lc), labeled with digoxygenin to combed genomic DNA extracted from amniotic samples, or from any other sample containing cells of fetal origin.

For example, it will be possible to use an avidin-Texas Red (red color) revealing system for the control probe and an antidigoxygenin-FITC (green color) revealing system for the specific probe: the total length of the red hybridization signals observed in a given region of the surface, LT, and the total length of the green hybridization signals observed in the same region, or in an equivalent region of the surface, LC, therefore lead to the numbers Nt and Nc defined above.

The ratio Nc/Nt of close to 1 will indicate a normal genotype (2 chromosomes 21 for 2 chromosomes 1), whereas a ratio of close to 1.5 will indicate a trisomic genotype (3 chromosomes 21 for 2 chromosomes 1).

In general, a significant difference between Nc and the value expected for the number of genomes present which is deduced from Nt is the indication of the presence of a gene abnormality.

In the case of the screening of oncogenes or proto-oncogenes, the same method may be used: a control probe will be hybridized and revealed in red for example and a probe corresponding to the gene or to a portion of the gene searched out will be hybridized and revealed in green for example. After the measurements carried out as above, the Nc/Nt ratio will give the relative abundance of the gene compared with the frequency of two copies per diploid genome.

The aberrant methylation of the GpC islands which is frequently observed in many cancers (92% of colon cancers) can also be detected by the method according to the invention by reaction between the combed DNA and fluorescent antibodies directed against the methylated cytosines.

Indeed, the loss of the heterozygosity on chromosone 9p21 is one of the genetic impairments most frequently identified in human cancers. The tumor suppresser gene CDKN2/p16/MTS1 located in this region is frequently inactivated in many human cancers by homozygous deletion. However, another mode of inactivation has been reported which involves the loss of the transcription associated with a de novo methylation of GpC 5' islands of CDKN2/p16 in lung cancers, gliomas and carcinomas with desquamation of the head and of the neck. These aberrant methylations of the GpC islands also frequently occur in breast (33%), prostate (60%), kidney (23%) and colon (92%) cancer cell lines (J. G. Herman et al., (1995) Cancer Res., October 15, 55(20); 4525-30; M. M. Wales et al., (1995) Nature Med., June, 1(6): 570-607).

The precise location of the methylation areas on a gene is of a very great importance for understanding the mechanism of the development of cancer and for a possible "screening"

test. Molecular combing can detect, with an accuracy of a few kb, the location of such GpC islands involved in the development of cancer.

This technique which makes it possible to determine the copy number of a gene in a genome can also be used to detect the absence of a portion of the genome.

In the case of a pathology characterized by the deletion of a substantial portion of a chromosome, it is indeed sufficient to take, as target sequence, a clone contained in the deleted region, and as control sequence a clone outside this region. It is thereby possible to detect deletions of the size of a cosmid clone (30-50 kb) or greater.

If a sufficient density of combed molecules is available, it is possible to envisage detecting smaller deletions (a few kb), corresponding to a portion of the target sequence used. That is the reason why it is particularly advantageous to place, on the combed surface, at least about 10 copies of genome.

The statistical error on the Nc/Nt ratio is of the order of $1/\sqrt{Nc}+1/\sqrt{Nt}$. Advantageously, it is advisable to have, on the combed surface, a sufficient number of signals in order to have a statistical error of less than 20% on the Nc/Nt ratio. It is therefore important to have a large number of hybridized probes, typically Nc, Nt>100.

However, in practice, it is also possible to increase the accuracy of these measurements by using not one but several types of control probes and target probes without necessarily seeking to distinguish between these types of probe, that is to say by revealing all of them in the same manner.

The possibility of obtaining such a number of signals has been demonstrated: it is possible to determine about one hundred signals on a silanized glass surface having a useful surface area of 20×20 mm. This density may be considerably increased as long as a large quantity of DNA is available.

It appears that a sufficient number of genome per surfaces having a useful surface area of 20×20 mm is in the region of 100, when a single probe is used. In the case where several probes or larger probes are used, it is possible to envisage being able to reduce either:

the combing surface and therefore the surface analyzed,
the DNA density used, and therefore the number of combed genomes at the surface.

Depending on the main constraint (speed required, or DNA in a limited quantity), either of these two routes may be used).

The technique disclosed involves the use of preparation protocols which are strict but without particular technical difficulties. At the level of the analysis of the signals, no particular qualification is necessary, thereby making the technique generalizable to all laboratories possessing staff with minimal competence in molecular biology.

A few hundreds of thousands of cells should in principle be sufficient to prepare a genomic DNA solution leading to a high density of combed molecules on the surfaces for analysis. It is therefore in principle no longer necessary to carry out cell cultures in most cases. It should therefore be possible to carry out the sampling-analysis as a whole within a few days.

The simplicity of the signals to be analyzed (which are parallel and distinct from the hybridization background noise) makes it possible to envisage complete automation of the process of analyzing the signals (scan of the surfaces, acquisition and processing of the measurements). Integration with a system for storing surfaces corresponding to various patients makes it possible to envisage high yields, giving the possibility of providing various types of diagnosis within a few days.

The method described above can allow various types of diagnosis: chromosome counting (trisomy, monosomy, and the like), counting of the copies of a gene, detection of known deletions, or other chromosomal modifications resulting in a modification of the hybridized length of a given genomic probe per genome.

It should be noted that it is also possible to detect a partial deletion on a single allele.

It is likewise possible to carry out the hybridization of clones on several different genomes combed on the same surface. For example, the simultaneous combing of the genome of a principal organism and of the genome of host organisms (parasites, bacteria, viruses and the like) and the use of specific probes, on the one hand from the principal organism and, on the other hand from host organisms, makes it possible in principle to determine the ratio number of hosts/number of cells of the principal organism. In the case of an organism infected by a virus, this allows the measurement of the viral load. The figures cited above probably limit the sensitivity of this method of diagnosis to situations where more than one infectious organism exists per 100 host cells approximately.

These various types of diagnosis may be combined by virtue of the use of multiple revealing systems (several colors, or combination of colors), or any other method allowing the distinction between the hybridization signals obtained from distinct probes and intended for a precise diagnosis.

The present invention also relates to diagnostic "kits" containing at least one of the following components:
a combing surface,
probes which are labeled or which are intended to be labeled, corresponding to the abnormalities to be detected,
a device allowing the combing of the DNA,
a control genome and/or control probes, said genome being optionally attached to the surface to be combed,
one or more specific results obtained using the preceding protocols in one or more control situations, so as to provide a grid for the interpretation of the results obtained in the diagnoses carried out, for example in the form of an expert system (software for example),
an expert system which makes it possible to facilitate the carrying out of diagnoses according to the method of the invention.

The principle of the technique being based on the combing of the patient's DNA, this DNA preparation step requires protocols for extraction, combing and the corresponding material (treated surfaces, molecular combing apparatus).

The subject of the invention is also a genomic DNA or a portion of genomic DNA capable of reacting, under molecular combing conditions, with a probe corresponding to a product of transcription or of translation or of regulation.

The diagnosis itself requires the hybridization of specific nucleotide probes and the revealing of these probes, for example by antibody systems. Given that a color coding can, in addition be carried out in the case of combined diagnoses, it is therefore possible to provide batches of prelabeled probes corresponding to a catalog of particular diagnoses.

Given that the analysis requires the measurement of the length of the signals or more generally of one of the three categories of information described above, a system for analyzing these signals (software and automated equipment) also forms part of this invention.

In a third embodiment, the present invention relates to a method allowing in particular the physical mapping of a genome.

The aim of physical mapping being the ordering of a clone within a genome, molecular combing naturally applies to this objective, by simple hybridization of the clones on the combed genome (for example, in the case of a YAC, the whole yeast genome may be combed, so as to dispense with the separation of the artificial chromosome from the natural chromosomes of the yeast).

The position of the clones is obtained by direct measurement of their distance to a reference clone, or to any other reference hybridization signal on the combed genome. The constant extension of the combed DNA then makes it possible to directly establish in kilobases (kb) the respective position of the clones as well as their size, when the latter exceeds the resolution of the method. In particular, in the case of conventional epifluorescence microscopy, whose resolution is half a wavelength, the precise mapping of cDNA (DNA complementary to the RNAs transcribed in the cell) is possible, but without the possibility of accurately measuring the size of the hybridized fragments (exons), which is of the order of a few hundreds of bases in general. However, using this method, the precise location within the genomic DNA of complete cDNA fragments or of their fragments may be obtained. For example, it is possible to determine the presence or the absence and the position of the cDNAs corresponding to a protein of interest by hybridization of the cDNAs to the genomic DNA or to a genomic DNA clone (cosmid, BAC, YAC, for example) at the same time as a clone serving as a reference mark.

The use of multiple fragments obtained from a cDNA leads to the picking out of the presence or otherwise of one or more genomic DNAs in a vector of the cosmid or YAC type for example.

The use of more resolutive methods may allow an additional measurement of the size of the probes (close field, electron microscopy, and the like), but a measurement of the intensity of fluorescence, if it is the mode of observation chosen, may also provide this information.

The method which we are providing makes it possible to minimize the number of hybridizations necessary for ordering a given number of clones, given a fixed number of colors for revealing the hybridizations, or (more generally) of distinct modes of revealing the hybridizations.

The invention relates to a method, characterized in that:
(a) a certain quantity of said genome is attached to and combed on a combing surface,
(b) the combing product is hybridized with probes labeled with radioactive or fluorescent elements and the like, such as beads, particles and the like, corresponding to each clone, such that said probes may be specifically revealed by a color in particular,
(c) the information corresponding to the position of each clone as well as the sizes and the corresponding distances on the genome are extracted,
(d) operations b) and c) are repeated n times by modifying the color, the labeling or the mode of revealing the probes, in the knowledge that with p colors, labelings or different modes of revealing, it is possible to position $p^n$ clones after n hybridizations.

In the context of the standard methods of mapping, the number I of hybridizations necessary to map N clones with the aid of p labelings, colors or modes of revealing, increases linearly with the number of clones N.

Thus, with 3 colours it is nowadays necessary to carry out at least 15 hybridizations of the preceding type in order to map 30 clones.

This number of hybridizations is high, and the number of available colors is in practice limited (even using combinations of fluorophores). Moreover, once all the measurements have been carried out, it is necessary to carry out the selection of the various possible positions of the clones, which may not always be easy, if the measurement errors are taken into account.

The method provided here makes it possible to map a number of clones which increases exponentially with the number of hybridizations carried out.

By way of illustration, the diagram in FIG. 10 represents the result of two hybridizations of 4 clones revealed with two different colors from one hybridization to another (for half of them). The 4 hybridized clones form a differently colored canvas from one hybridization to another, it being possible to pick out the clones via their coding (binary in this case). In this example of 4 clones, a code composed of a succession of 2 colors is sufficient to distinguish each clone:
A=Red then Red
B=Green then Green
C=Red then Green
D=Green then Red From 5 to 8 clones, 3 hybridizations will be necessary, in order to distinguish between the clones by a succession of 3 colors.

More generally, using p colors, to map N clones, a number of hybridizations I such that: $N=p^I$ will be sufficient.

In comparison -with the standard method, 30 clones may be mapped in 5 hybridizations (instead of 30) if only 2 colors are available, and in only 4 hybridizations (instead of 15) if 3 colors are available.

The mapping principle presented here is simple. However, in order to overcome certain possible experimental artefacts (dispersion of the sizes of the signals, variability of saturation, break in the molecules and the like), suitable software for processing images and for statistical analysis will be advantageously used.

The examples below will make it possible to better understand other characteristics and advantages of the present invention.

Finally, in a fourth embodiment, the present invention relates to a method allowing in particular the detection or the location of products capable of reacting with the combed DNA. For example, proteins for regulating the transcription of a DNA-binding gene during the cell cycle or otherwise may be detected on combed DNA, and their preferred binding sites determined relative to the position of sequences which are known and which have been picked out, for example, according to the preceding method for carrying out the invention.

In a similar manner, molecules of therapeutic interest which are capable of reacting with DNA may be detected on combed DNA; their effect on other molecules capable of reacting with DNA may also be studied by comparison.

Among the molecules capable of reacting with the combed DNA, there should be mentioned regulatory proteins as described by:
Laughon and Matthew (1984), Nature, 310: 25-30 for the regulatory proteins which attach to the drosophile DNA,
K. Struhl et al. (1987), Cell, 50: 841-846 for regulatory proteins which bind to DNA in their specific binding domain.

These molecules may also be intercalating agents or molecules which modify DNA as described by:
H. Echols et al., (1996), Science, 223: 1050-1056 on the multiple interactions of DNA inducing, for example, transcriptions;

in the review An. Rev. of Bioch. (1988), 57,: 159-167, Gross and Ganard describe the hypersensitivity of nuclease sites in chromatin;

Hanson et al., (1976), Science, 193: 62-64 describe psoralen as a photoactive agent in the selective cleavage of nucleotide sequences;

Cartwright et al. (1984), NAS, 10: 5835-5852.

The invention also relates to any molecule, solvent or method linked to a parameter identified by one of the methods described above in accordance with the invention.

(a) Situation in a healthy patient (b1) Deletion(s) of a portion of the gene. (b2) Deletion of the entire gene.

(c1) and (c2) Translocation of a portion of the gene.

(c3) Translocation of the entire gene.

(d1) Duplication(s) of a portion of the gene (optionally with inversion). (d2) Duplication(s) of the entire gene (optionally with inversion). (d3) Repetition(s) of a portion of the gene in another portion of the genome. (e) Insertion(s) into the gene, of a different portion of the gene (and of the cloned genome).

Figure 1A:
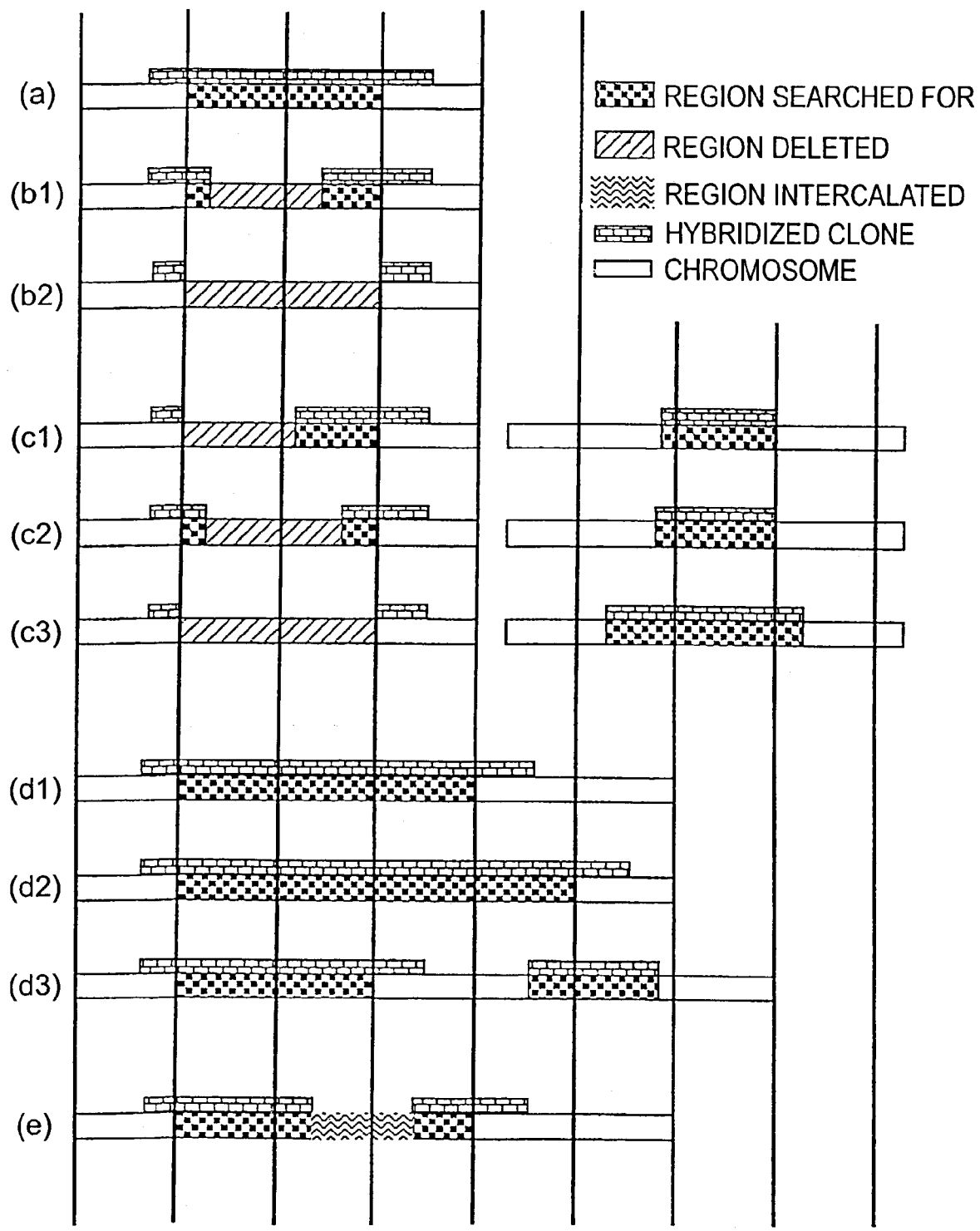
FIG. 1a: Illustration of the case of a clone (red) overlapping the gene (and therefore the break point) searched out. The hashed regions should be thought of as being absent, which means in particular that when two segments of probes exist side by side, they in fact form only one segment having a length equal to the sum of their lengths. The subadjacent chromosome(s) is (are) represented by white bars.
Figure 1B:
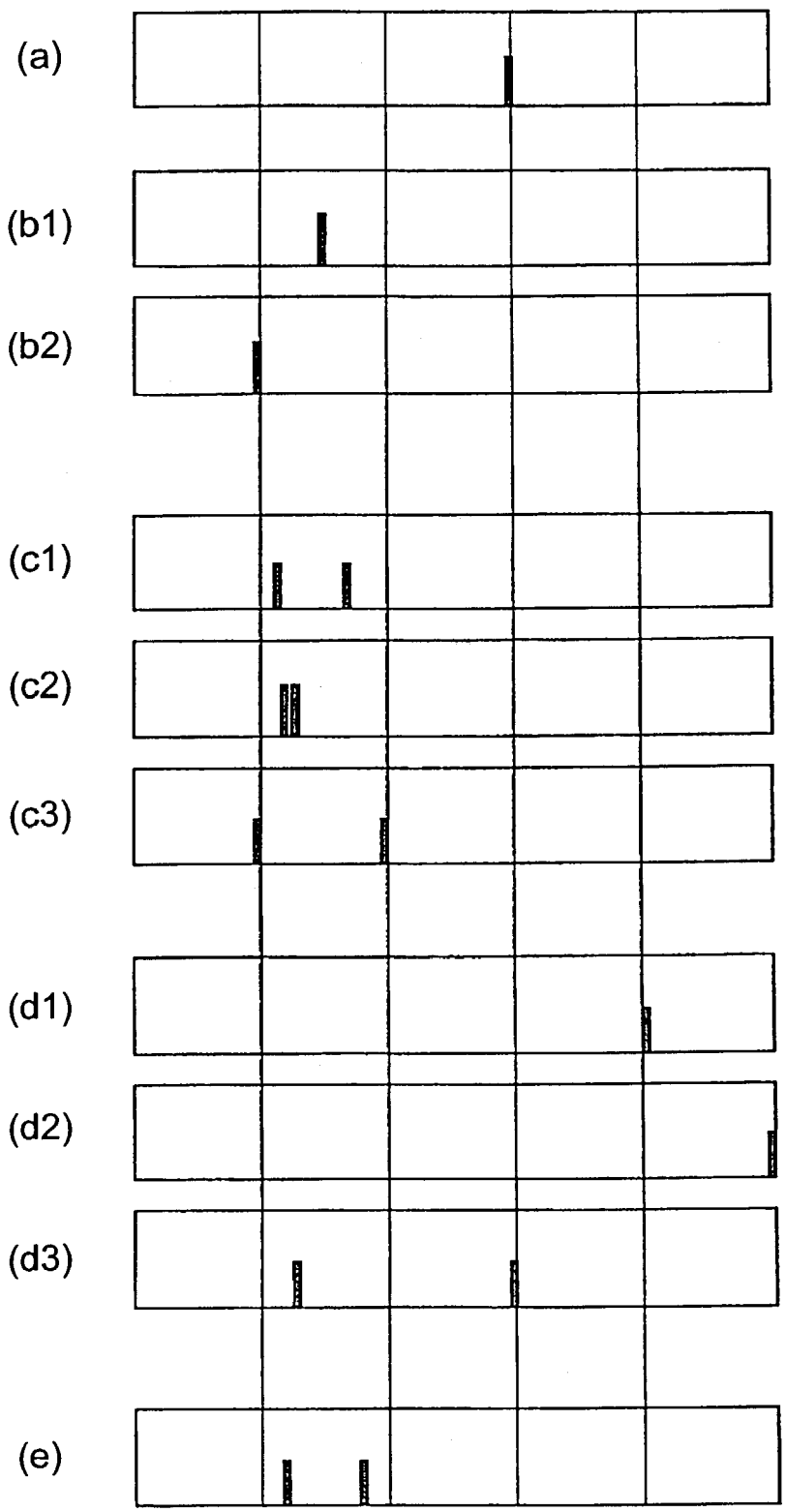

FIG. 1b: Ideal histograms of the lengths of hybridized clones corresponding to the preceding situations. In all cases (one or two peaks), the situation is clearly distinguishable from that of the whole clone (a).

Figure 1C:
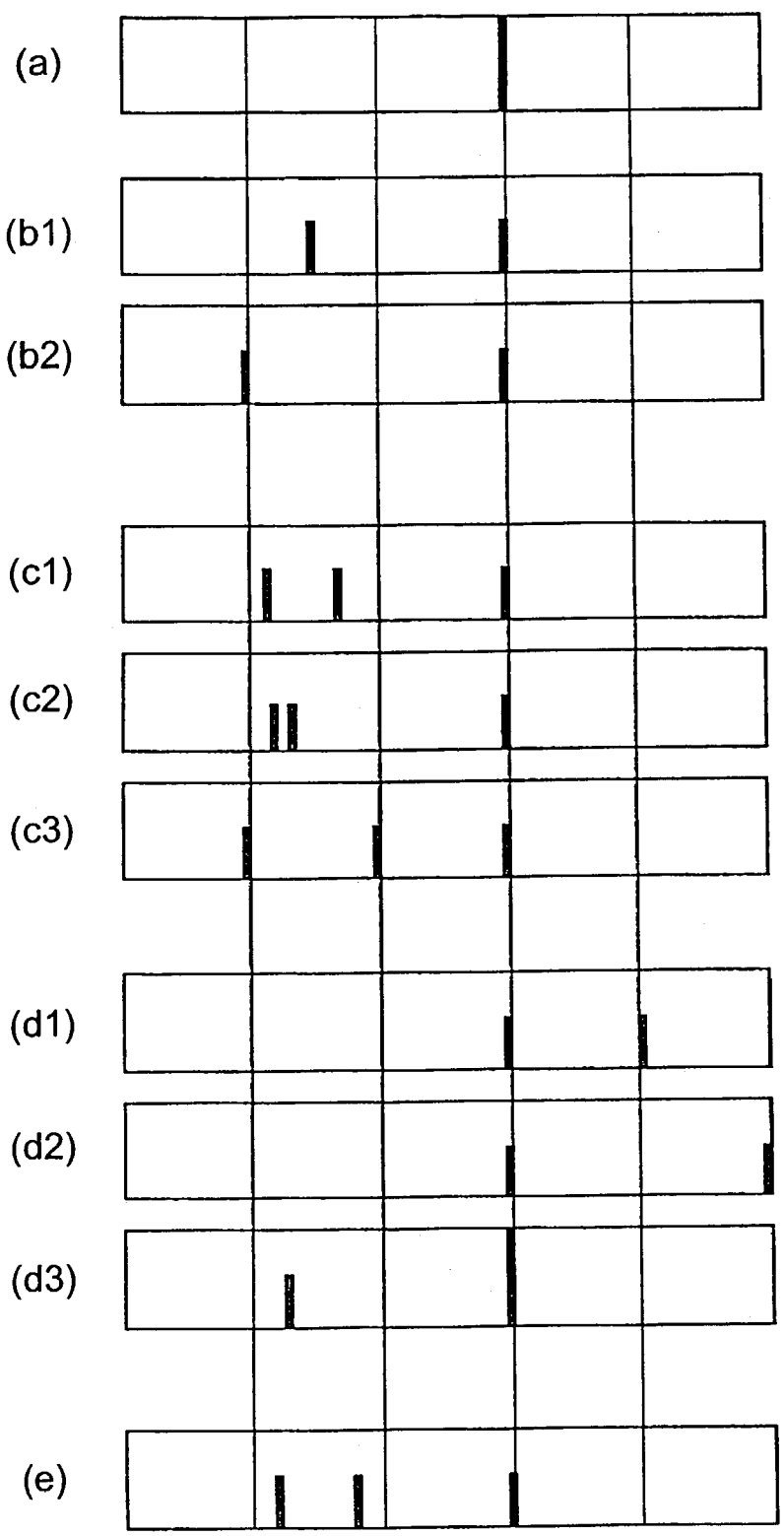

The histograms of this figure correspond to the signals of the abnormal allele and are therefore obtained after subtraction of the contribution due to the normal allele, represented in (a), from the crude histograms, represented in FIG. 1c. On the x-axis is the size of the hybridized fragments, the (arbitrary) scale being the same as that of FIG. 1a. On the y-axis is the number of fragments observed, in arbitrary units, only the proportions between the various populations being important.

FIG. 1c: Ideal histograms of the lengths of hybridized clones corresponding to the preceding situations and taking into account the normal allele. The contribution of the normal allele is represented by the peak corresponding to the position of the normal case represented in (a). When the abnormal allele contributes towards increasing the value of this peak (case (d3)), the contribution of the normal allele may in general be considered to be equivalent to the value of an abnormal peak.

Figure 2A:
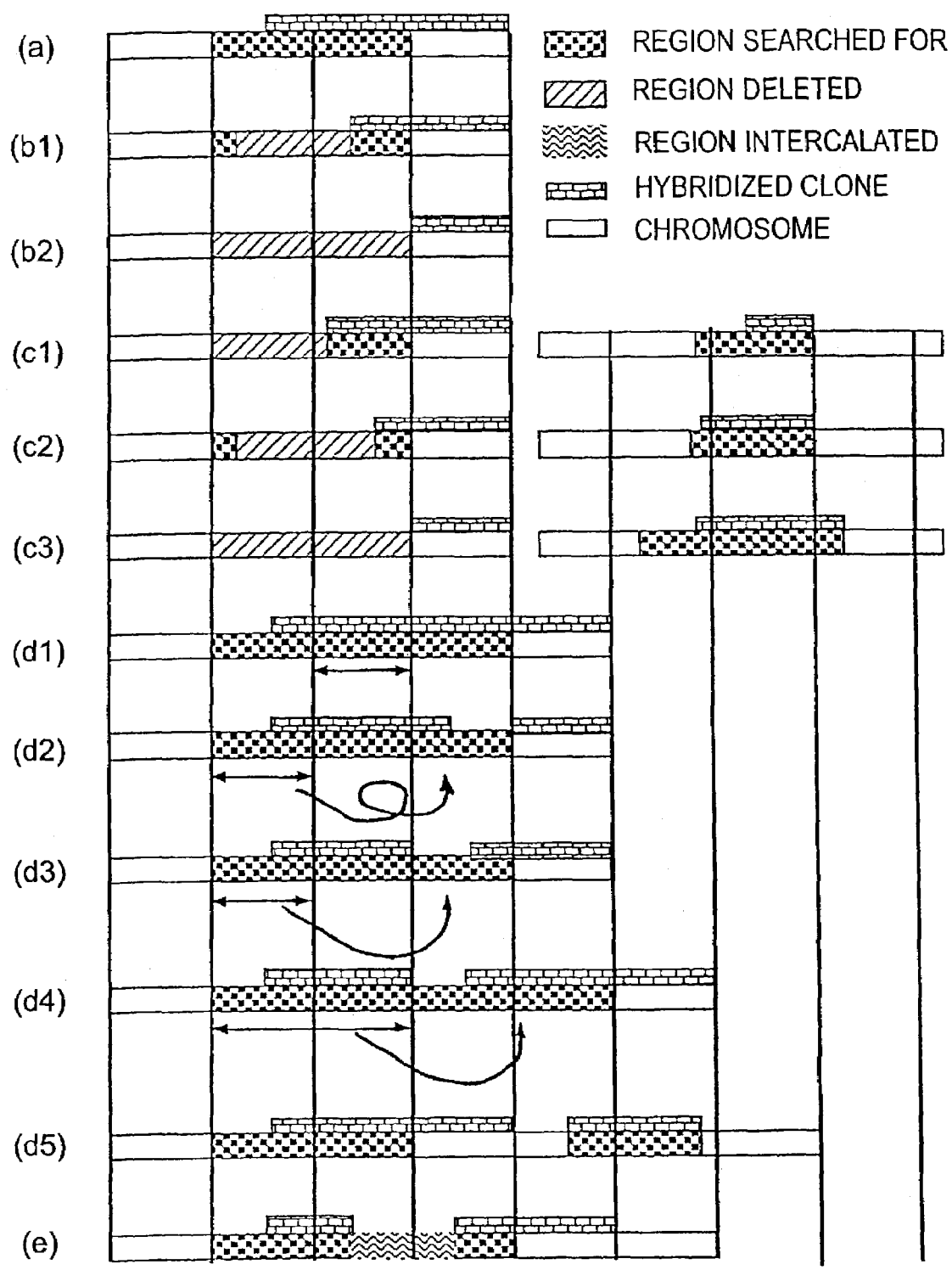

FIG. 2a: Illustration of the case of a clone partially overlapping the gene searched out.

(a) Situation in a healthy patient.

(b1) Deletion(s) of a portion of the gene. Another situation was not represented, where the deleted portion is fully included in the clone (cf. case corresponding to diagram 1a).

(b2) Deletion of the entire gene.

(c1) and (c2) Translocation(s) of a portion of the gene. Another situation, corresponding to case (c2) of diagram 1a was not represented, where the translocated portion is fully included in the clone.

(c3) Translocation(s) of the entire gene.

(d1) Duplication(s) of a portion of the gene marked by a double-headed arrow (the duplicated portion is fully included in the clone). (d2) Duplication(s) of a portion of the gene with inversion. (d3) Duplication(s) of a portion of the gene (the duplicated portion is partially included in the clone).

(d4) Duplication(s) of the entire gene (without inversion).

(d5) Repetition(s) of a portion of the gene in another portion of the genome.

(e) Insertion(s) into the gene of a different portion of the gene (and of the genome cloned).

Figure 2B:
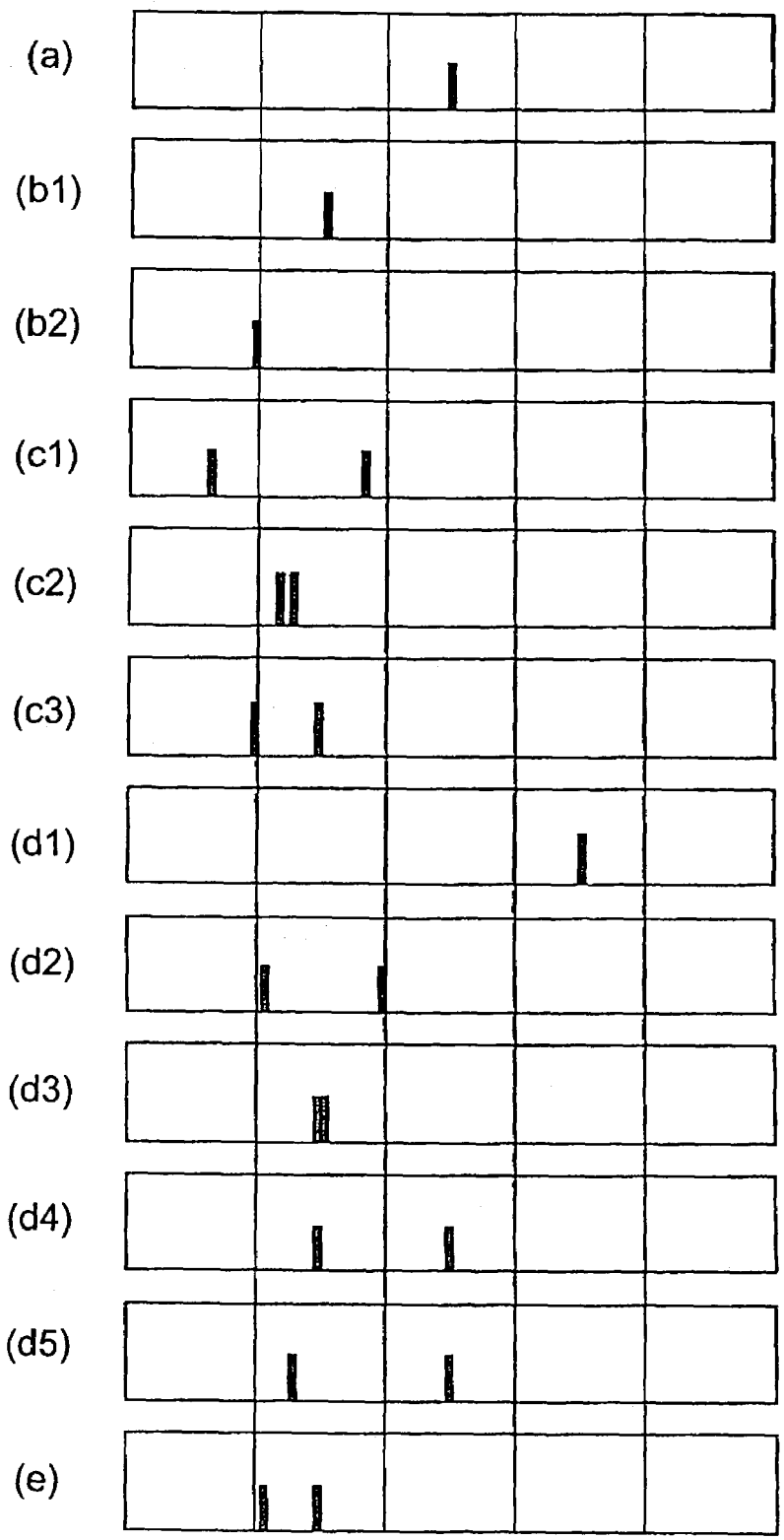

FIG. 2b: Ideal histograms of the lengths of hybridized clones corresponding to the preceding situations. In all cases (one or two peaks), the situation is clearly distinguishable from that of the whole clone (a).

Figure 2C:
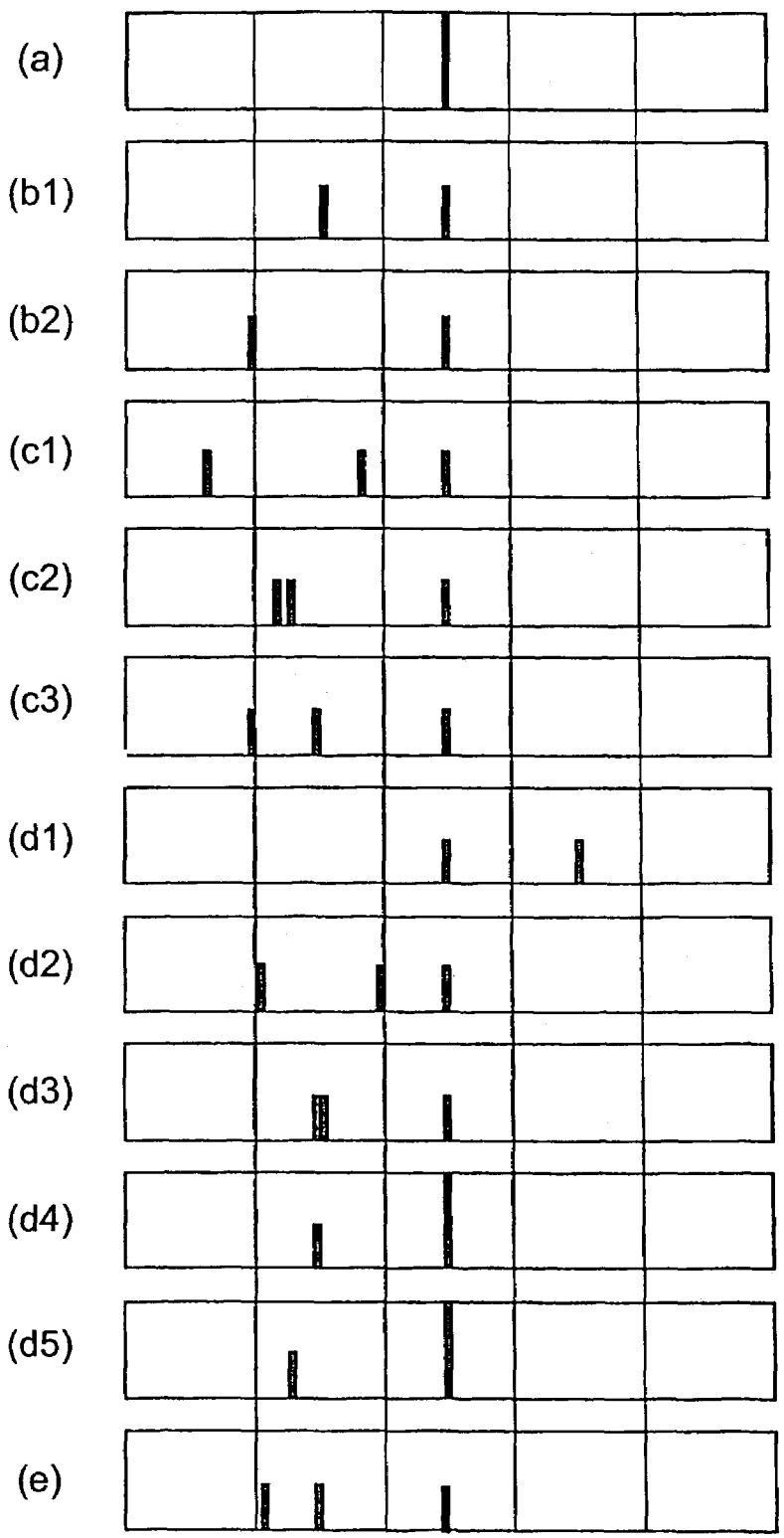

The histograms of this figure correspond to the signals of the abnormal allele and are therefore obtained after subtraction of the contribution due to the normal allele, represented in (a), from the crude histograms, represented in FIG. 2c. On the x-axis is the size of the hybridized fragments, the (arbitrary) scale being the same as that of FIG. 2a. On the y-axis is the number of fragments observed, in arbitrary units, only the proportions between the various populations being important.

FIG. 2c: Ideal histograms of the lengths of hybridized clones corresponding to the preceding situations and taking into account the normal allele. The contribution of the normal allele is represented by the peak corresponding to the position of the abnormal case represented in (a). When the normal allele contributes towards increasing the value of this peak (cases (d4) and (d5)), the contribution of the normal allele may in general be considered to be equivalent to the value of an abnormal peak.

Figure 3A:
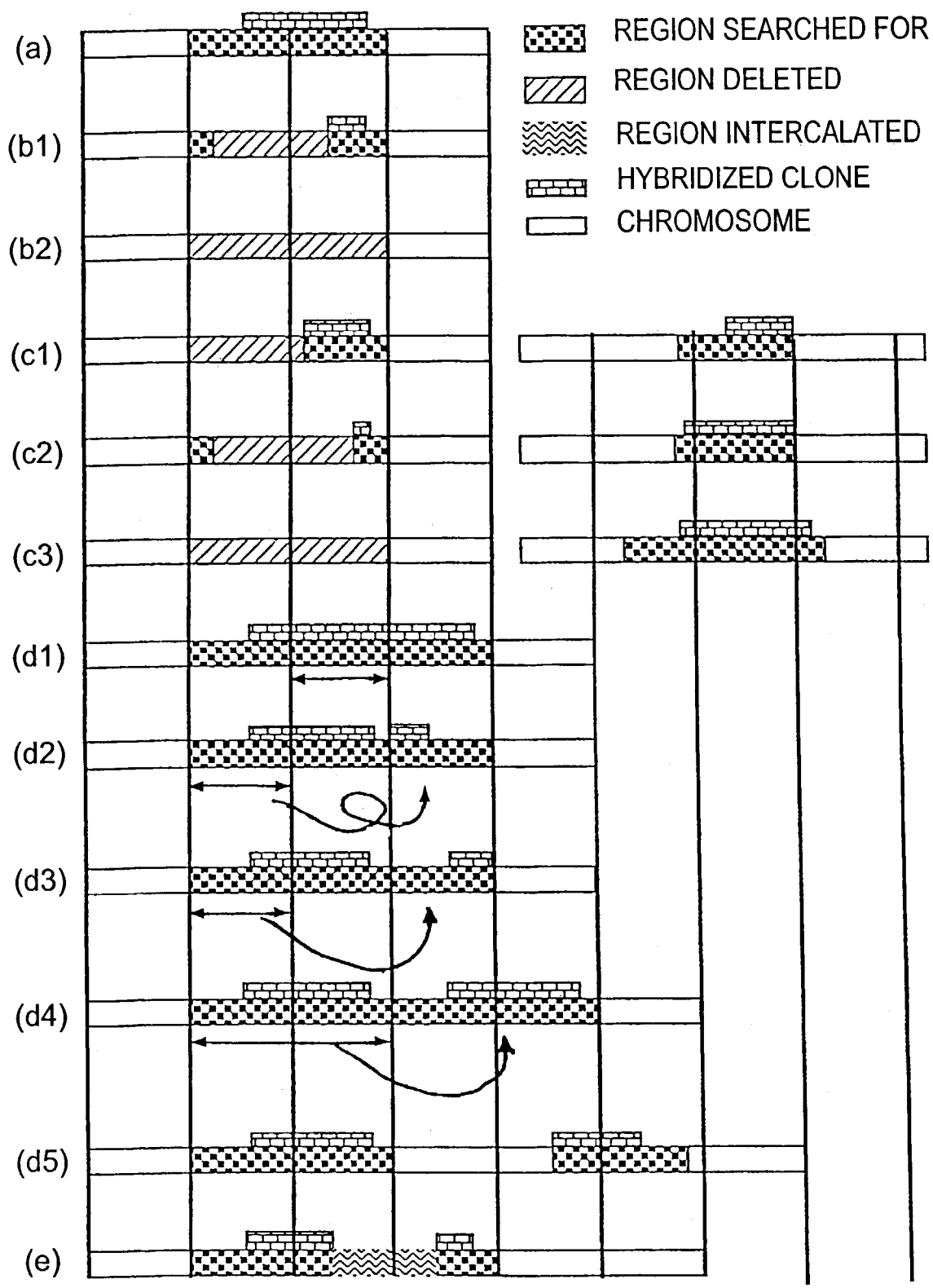

FIG. 3a: Illustration of the case of a clone completely included in the gene searched out.

(a) Situation in a healthy patient.

(b1) Deletion(s) of a portion of the gene. Another situation was not represented, where the deleted portion is fully included in the clone (cf. case corresponding to diagram 1a).

(b2) Deletion of the entire gene.

(c1) and (c2) Translocation(s) of a portion of the gene. Another situation, corresponding to case (c2) of diagram 1a was not represented, where the translocated portion is fully included in the clone.

(c3) Translocation(s) of the entire gene.

(d1) Duplication(s) of a portion of the gene marked by a double-headed arrow (the duplicated portion is fully included in the clone). (d2) Duplication(s) of a portion of the gene with inversion. (d3) Duplication(s) of a portion of the gene (the duplicated portion is partially included in the clone).

(d4) Duplication(s) of the entire gene (without inversion).

(d5) Repetition(s) of a portion of the gene in another portion of the genome.

(e) Insertion(s) into the gene of a different portion of the gene (and of the genome cloned).

Figure 3B:
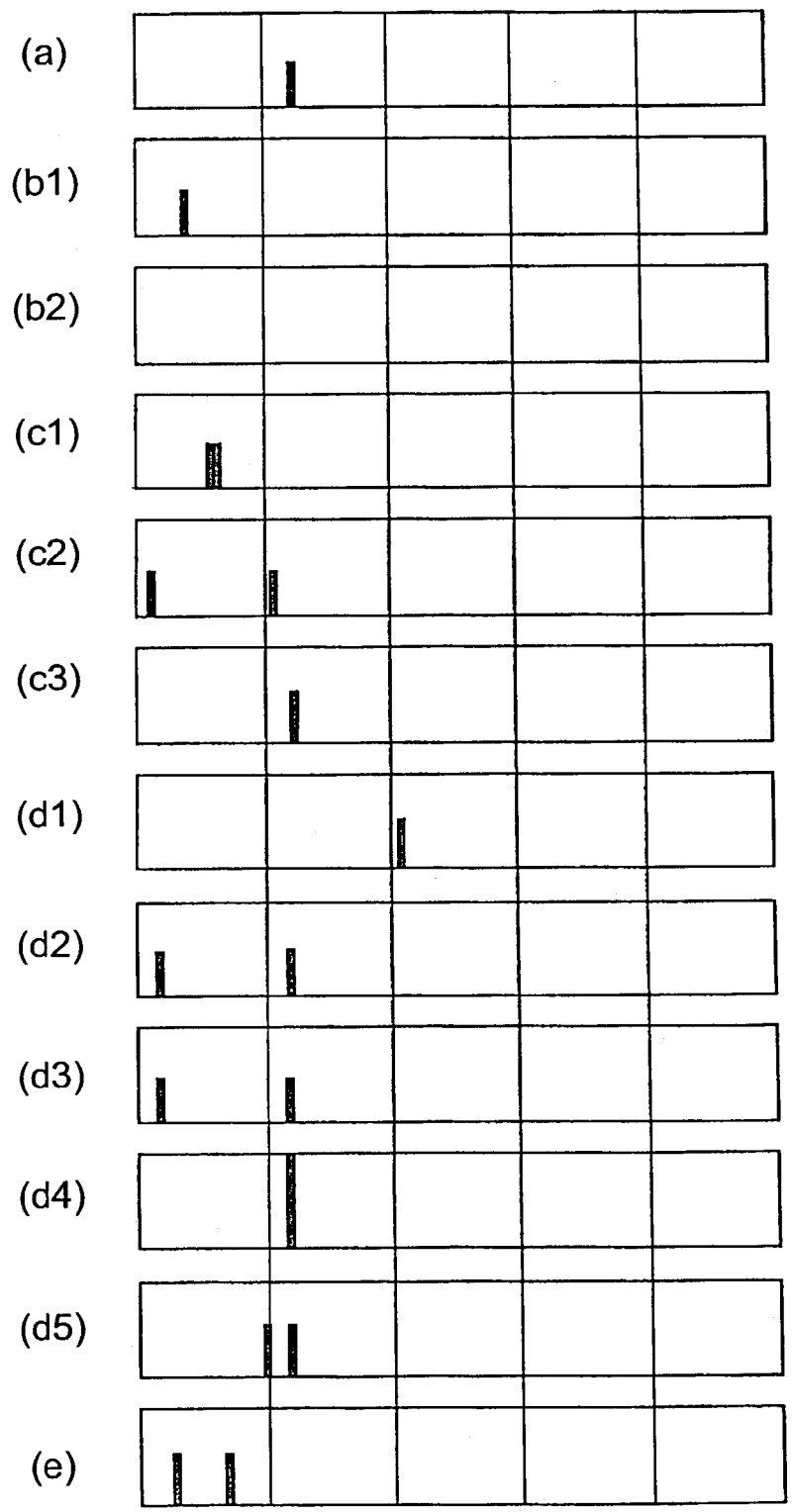

FIG. 3b: Ideal histograms of the lengths of hybridized clones corresponding to the preceding situations. In all cases (one or two peaks), the situation is clearly distinguishable from that of the whole clone (a).

Figure 3C:

The histograms of this figure correspond to the signals of the abnormal allele and are therefore obtained after subtraction of the contribution due to the normal allele, represented in (a), from the crude histograms, represented in FIG. 3c. On the x-axis is the size of the hybridized fragments, the (arbitrary) scale being the same as that of FIG. 3a. On the y-axis is the number of fragments observed, in arbitrary units, only the proportions between the various populations being important.

FIG. 3c: Ideal histograms of the lengths of hybridized clones corresponding to the preceding situations and taking into account the normal allele. The contribution of the normal allele is represented by the peak corresponding to the position of the normal case represented in (a). When the abnormal allele contributes towards increasing the value of this peak (cases (c3), (d2), (d3) and (d5)), the contribution of the normal allele may in general be considered to be equivalent to the value of an abnormal peak.

Figure 4:
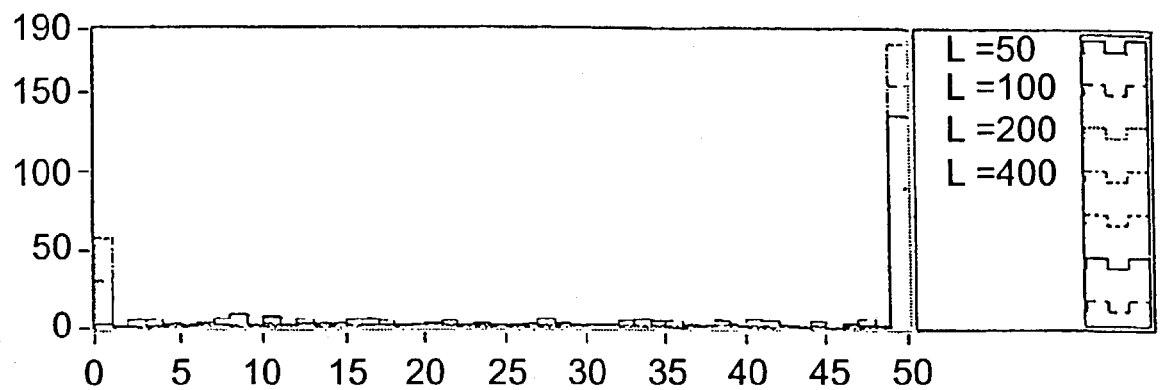
Figure 4:
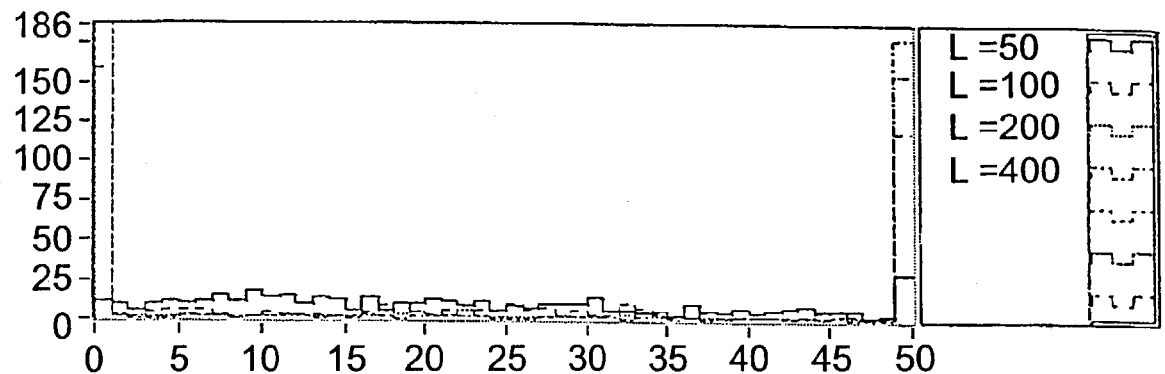
Figure 4:
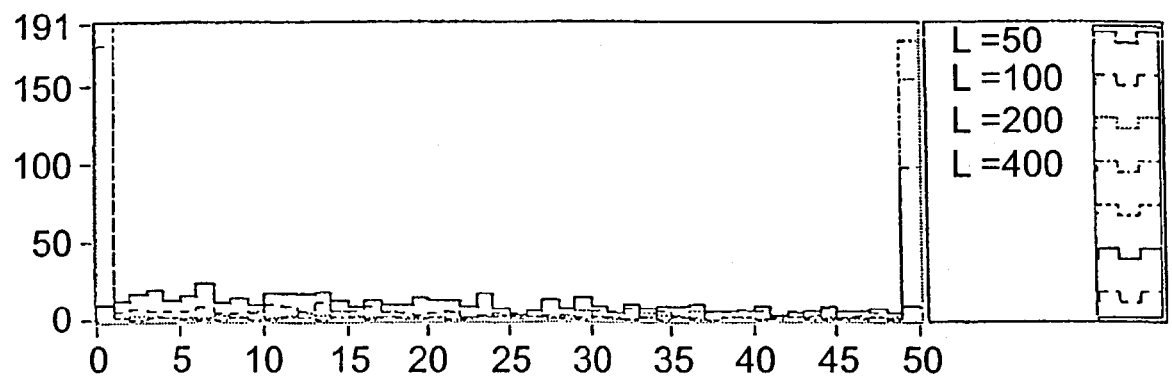

FIG. 4: Histograms of the lengths of the step model. Study of the influence of the characteristic size.

Figure 5:
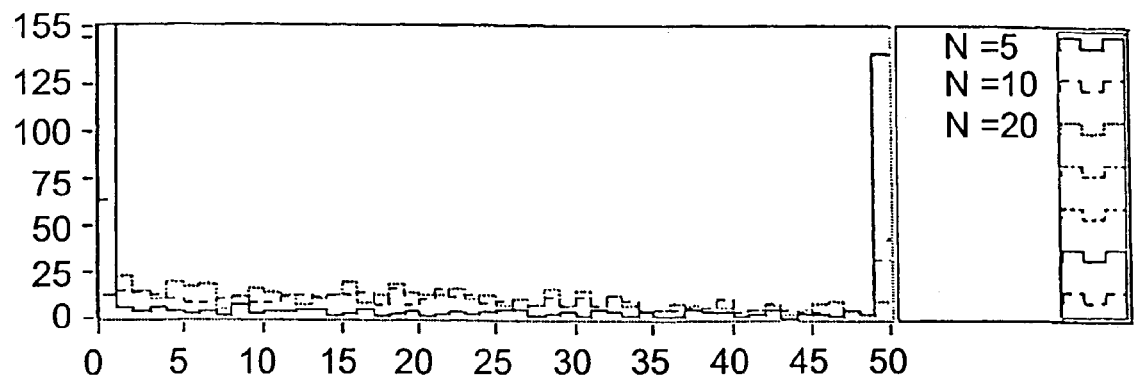
Figure 5:
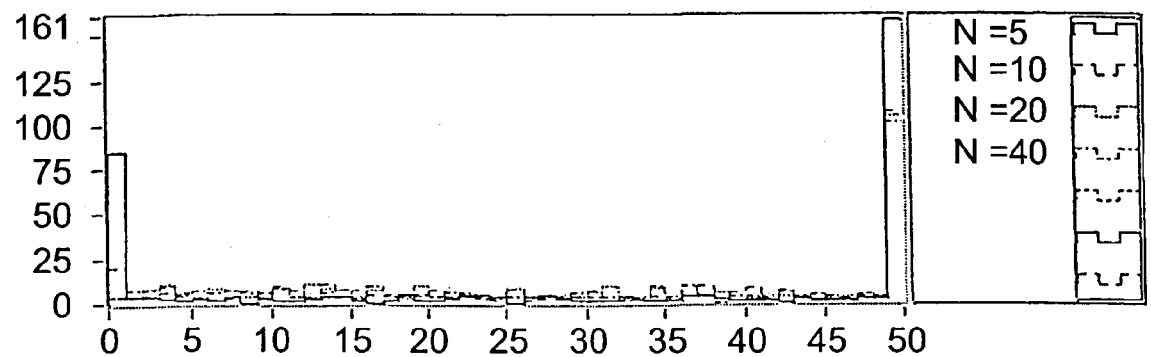
Figure 5:
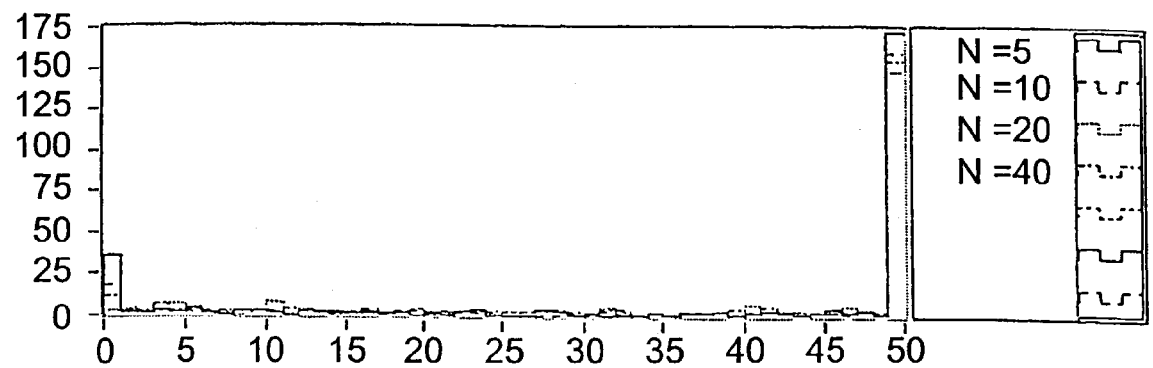

FIG. 5: Histograms of the lengths of the step model. Study of the influence of the break level.

Figure 6:
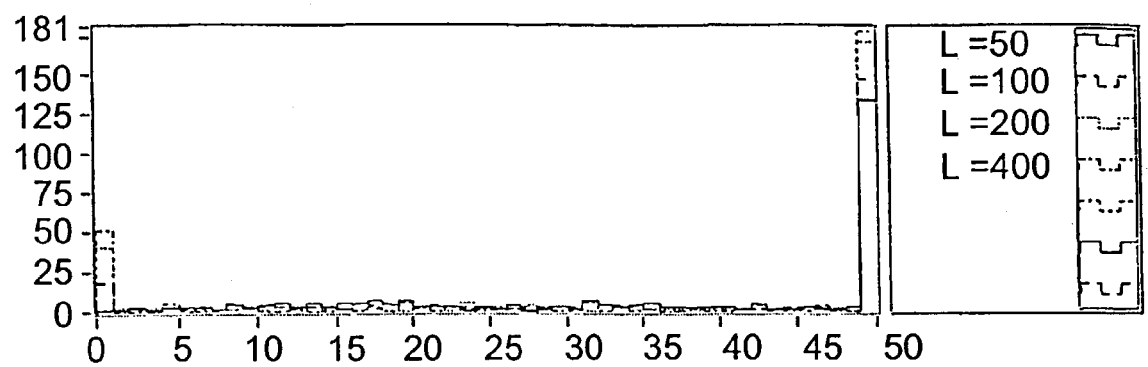
Figure 6:
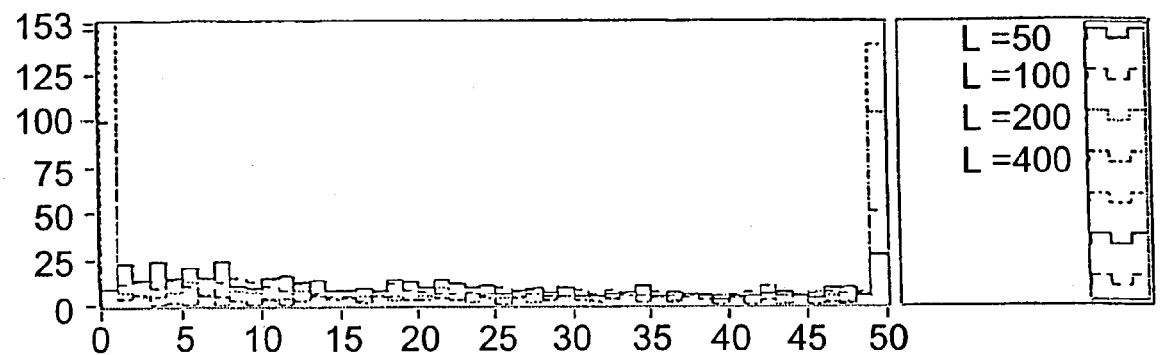
Figure 6:
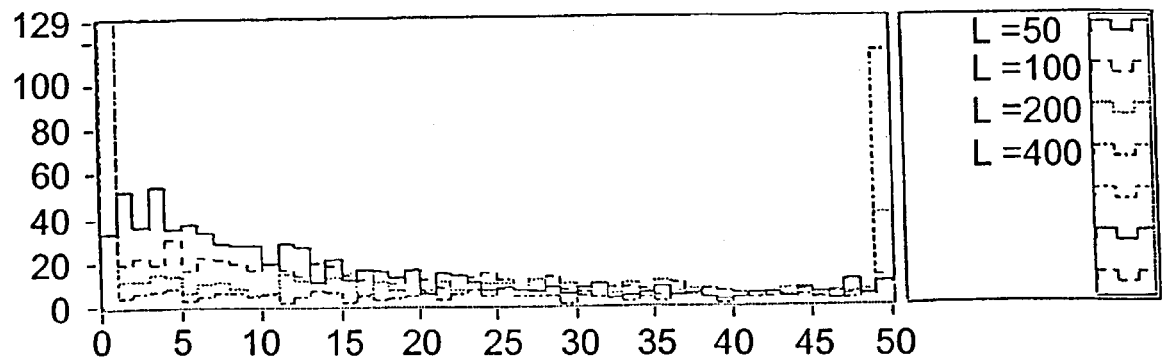

FIG. 6: Histograms of the lengths of the Gaussian model. Study of the influence of the characteristic size.

Figure 7:
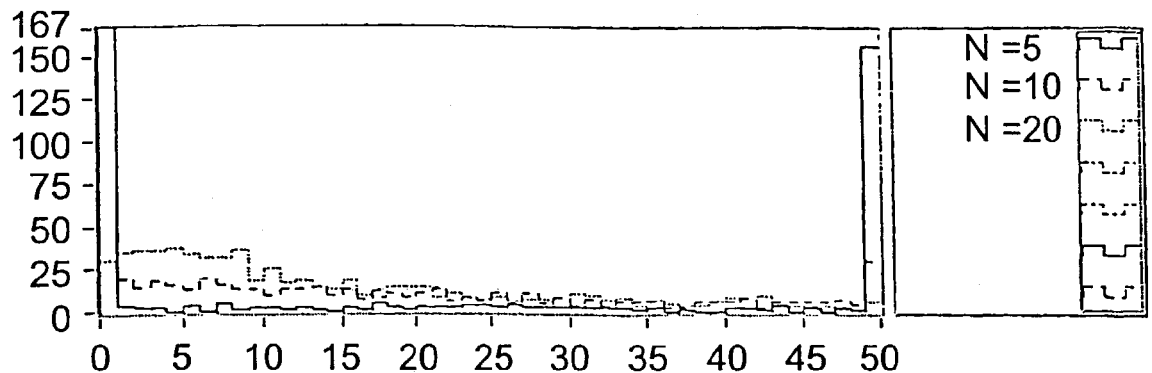
Figure 7:
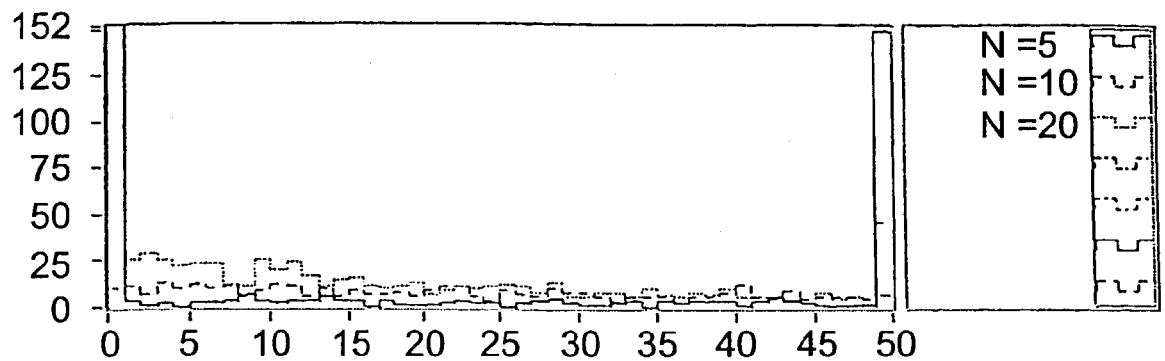
Figure 7:
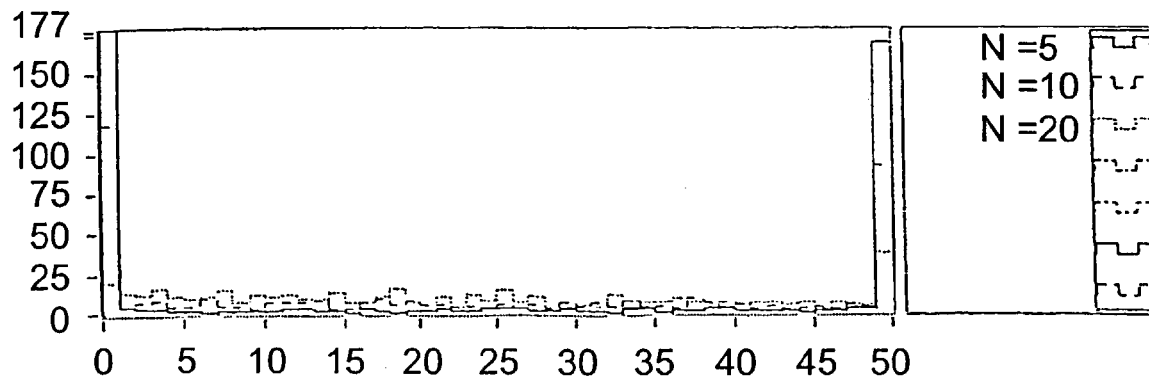

FIG. 7: Histograms of the lengths of the Gaussian model. Study of the influence of the break level.

FIG. 8: Simulation of histograms in the case of the hybridization of a BAC (125 kb) on a break point:

(a) fragments of 35 and 90 kb; (b) fragments of 50 and 75 kb; (c) fragments of 60 and 65 kb, (d) control situation; (e) real histogram of a contig of cosmid clones hybridized to human genomic DNA (length of the contig: about 77.5 μm, that is 155 kb). The x-axis represents the size of the fragments in microns. The y-axis represents the number of continuous fragments of hybridized probes.

Figure 9:
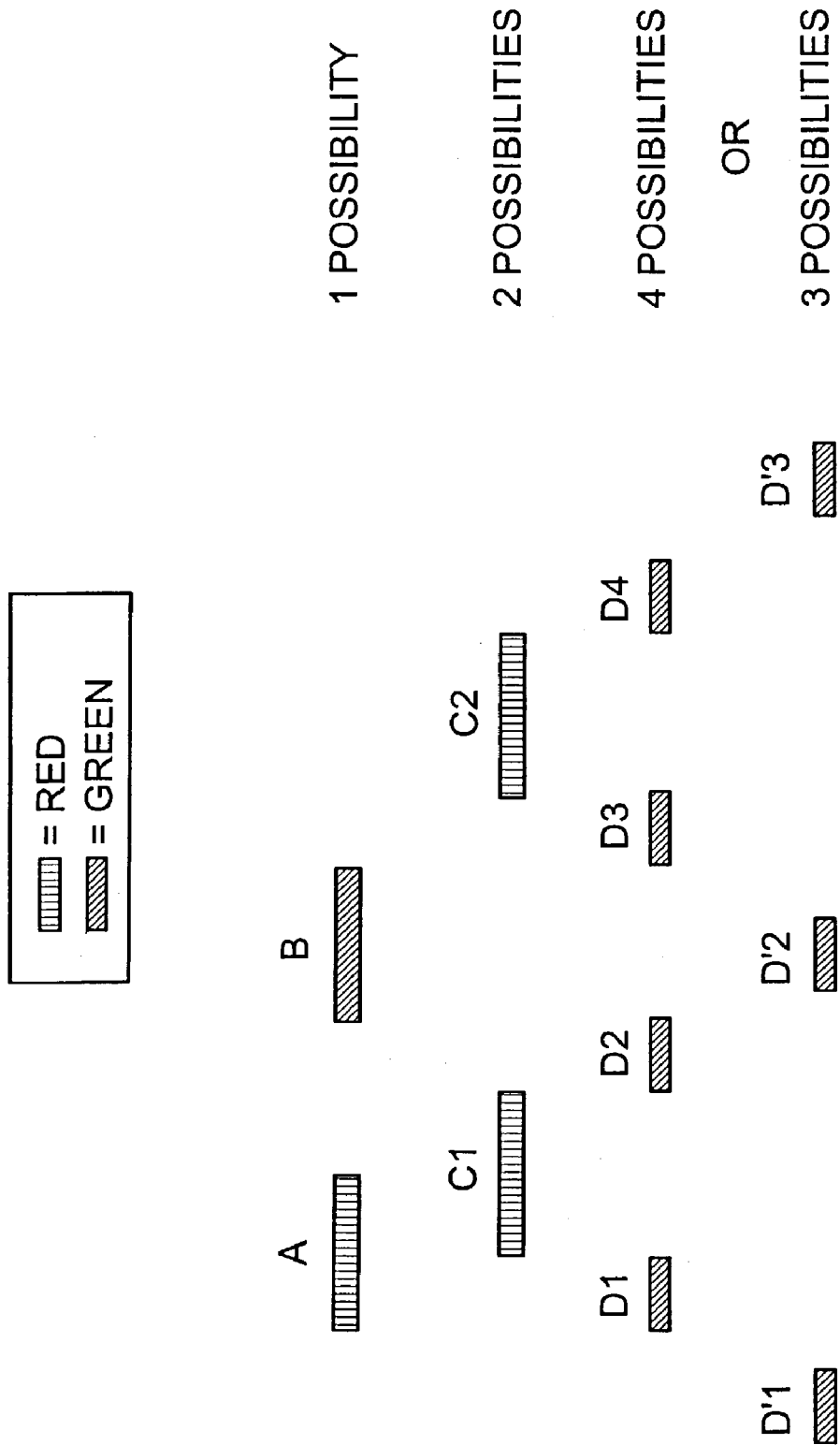

FIG. 9: Illustration of the principle of mapping without color coding. Each line represents the possible location of the new subclone mapped relative to that with which it is hybridized. The orientation of the first two clones is arbitrary. At each stage, two positions on either side of the old clone used are possible for the new hybridized clone.

Figure 10:
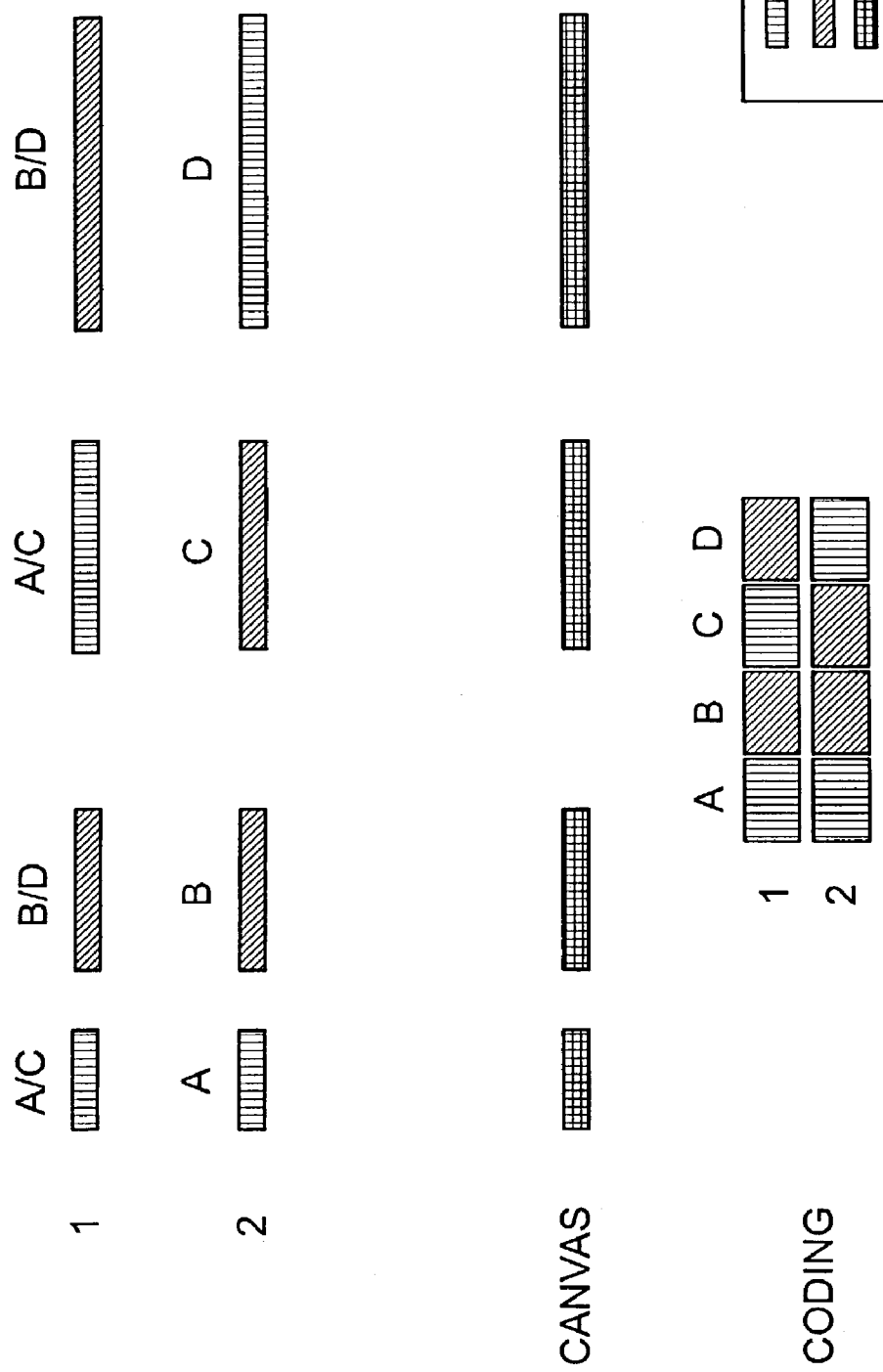

FIG. 10: Illustration of the principle of mapping with color coding.

At each hybridization, the same subclones are hybridized, giving rise to the same hybridization motif (canvas) if the color information is disregarded. The two palettes of color which are used make it possible to pick out without ambiguity each of the subclones (principle of coding).

Figure 11:
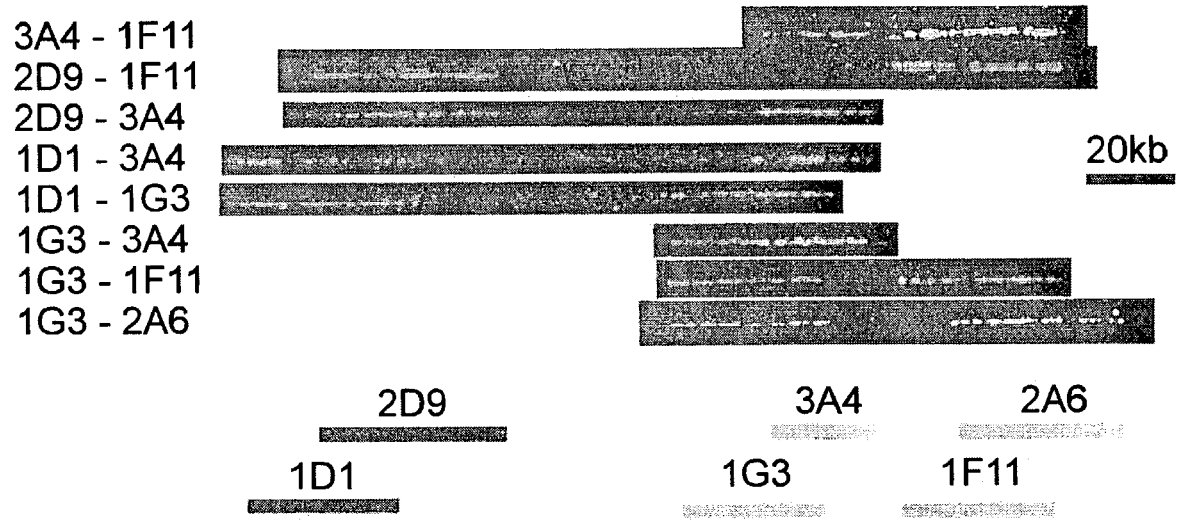

FIG. 11: Total genomic DNA of yeast containing an artificial chromosome (YAC774G4) was combed on treated surfaces. Cosmids belonging to two adjacent contigs separated by an unknown interval were hybridized in pairs so as to be able to reconstitute an accurate map of their arrangement. Among the cosmids used, 1F11 contains the majority of the sequence of the gene for calpain 3 whose mutations are responsible for girdle myopathy type 2A.

The figure shows images characteristic of each hybridization (a cosmid being hybridized and revealed in red, on the left, the other in green, on the right) as well as the map reconstituted from the measurements, to within approximately 3 kb. The scale is given by the 20 kb bar. This experiment made it possible in particular to correct a map of the region obtained with the aid of STSs (Richard et al., 1995, Mammalian Genome, 6, 754-756) and to obtain the chromosomal orientation of the gene.

Figure 12:
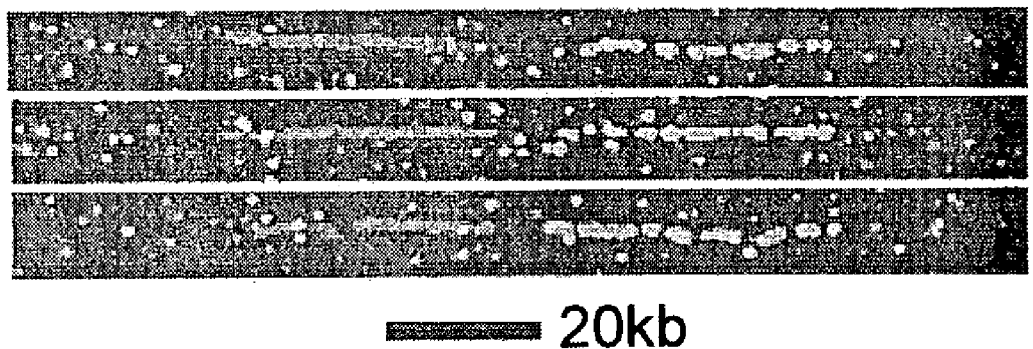
Figure 12:
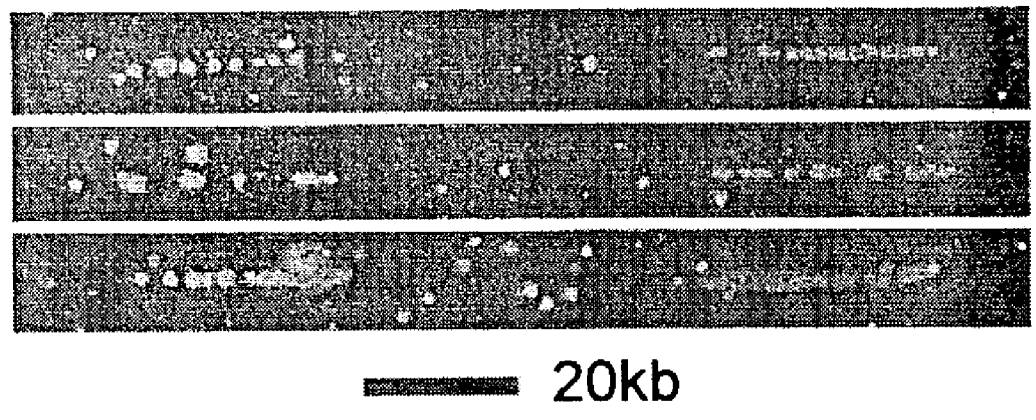

FIG. 12: Human total genomic DNA was combed on treated surfaces. Cosmids belonging to 3 adjacent contigs of the region of chromosome 9 containing the gene (not cloned) for "Tuberous Sclerosis 1" (STC1) were hybridized in pairs and revealed in 2 different colors in order to measure the size of the intervals separating these contigs. The figure shows 3 images characteristic of each of these measurements giving the distances between cosmids with an accuracy of 1.5 to 3 kb for 50 to 80 measurements. The code for the cosmids used is indicated, as well as the contig to which they belong (in parentheses). The green color is represented in white and the red color in gray.

MATERIALS AND METHODS

Histogram Method

The diagram in FIG. 1a presents a number of situations in the case of a probe completely covering the region of the genome searched out (region containing any genomic sequence whose modification causes the appearance of a pathology). Preferably, the probe covers part of the genome not involved in the break, that is to say on either side of the deletion for example.

The corresponding theoretical histograms (on the assumption that the genomic DNA combed is intact, which is naturally not very realistic, and which will be discussed in the text which follows) are presented in the diagram of FIG. 1b. FIG. 1c represents the crude results before extracting the contribution of the normal allele. Similar situations are represented in the case where the clone used does not completely cover the gene (or the region of the genome) searched out on the diagrams of FIGS. 2a and 3a.

In the text which follows, the expression "this genome region" (meaning involved in the pathology) or "the gene" will be used interchangeably since the technique strictly speaking does not make it possible to determine a gene, but a region of the genome which is impaired (resulting in "a break point").

All the situations represented in the preceding diagrams give an idea of the expected difference between a situation where the cloned probe used hybridizes to a region of the genome of a healthy individual which is modified in the case of a diseased individual.

In all the cases presented (except that of a translocation of all or part of the gene containing the entire clone—cf. diagram 3a (c3)), the histogram (theoretical) is distinguishable from the "normal" histogram:

either by the presence of a single peak but which is situated at a value different from the length of the clone (higher—case (d2) for example, or lower—case (b1))

or by the presence of two peaks or more.

The simple data for the histogram of the lengths and of the length Lc of the clone (obtained for example with the aid of a hybridization on the DNA of a healthy individual and obtaining of the peak of the corresponding histogram) therefore makes it possible to know whether the clone studied covers a break point (in the broad sense meant here).

The abnormalities observed at the level of the histogram may be grouped into several categories:

(a) one peak for a length Li<Lc
(b) one peak for a length Ls>Lc
(c) several peaks shorter than Lc
(d) several peaks longer than Lc
(e) one peak for a length L=Lc and one or more peaks shorter than Lc
(f) one peak for a length L=Lc and one or more peaks longer than Lc
(g) one or more peaks of lengths <, =and >Lc The classes of abnormalities listed above are unfortunately generally not sufficient to define the underlying genetic abnormality.

The diagram of FIG. 1b indeed shows that it is not possible a priori to distinguish between a partial translocation (c1) or (c2), a complete translocation (c3) or an insertion in the case of a clone which would cover the entire gene.

The same applies for the case where the clone would only partially cover the gene (diagram of FIGS. 2*b* and 3*b*).

On the other hand, the data for the lengths corresponding to the peaks of the histogram makes it possible to specify in some cases the position, in the clone, of the end of the portion of the genome deleted, translocated, duplicated or in contact with an insertion.

In any case, the measurement of a histogram different from the one expected in the case of a normal genome indicates the presence, in the genome studied, of an abnormality at the level of the sequence contained in the clone used.

(a: one peak for a length Li<Le): this almost certainly involves one (or more) deletions. However, as has been noted, it may involve a case where several peaks are grouped together. We shall see that it is generally possible to distinguish between these two cases by comparison with a probe corresponding to a different region of the genome (reference probe).

In the case of a deletion, it is possible to deduce therefrom the size by subtracting the two remaining lengths from the length of the intact clone (only in the case where the clone covers the entire deleted portion of the gene). The position relative to the clone cannot however be known, given that only additional hybridizations with other clones or subclones can allow this determination.

However, the same type of histogram may correspond to several deletions, in which case it is only possible to measure the total size of the deletions (still on the assumption that the clone would cover the entire deleted portion of the gene).

In the case where the clone only partially covers the gene, the deletion detected may represent only a portion of the effective deletion of the gene (cf. diagram 2a (b1) for example).

(b: one peak for a length Ls>Lc): in this case, one or more duplications inside the gene or at its ends, of a portion or of the whole of said gene, are involved. The clone may completely or partially cover the gene. There may optionally be inversion of the sequences, but this cannot be detected in the case where the clone completely covers the gene. The position of the duplication(s) cannot be determined.

(c: several peaks shorter than Lc): partial translocations of the gene or the insertion of a sequence inside the gene may be involved in this case. Assuming a translocation, it is possible to specify the two ends of the gene within the clone (case where the clone completely covers the gene), or to put forward two possibilities for these ends (in the case where the clone partially covers the gene).

(d: several peaks longer than Lc): several duplications of all or part of the gene in the region of the genome covered by the clone may be involved in this case.

(e: one peak for a length L=Lc and one or more peaks shorter than Lc): one (or more) duplications of all or part of the gene in a region of the genome different from the region covered by the clone may be involved, this in the case where the clone covers the whole or a portion of the gene.

(f: one peak for a length L=Lc and one or more peaks longer than Lc): although this situation was not represented in diagrams 1 to 3, it involves a case of duplication of the (d) type associated with a normal gene.

(g: one or more peaks of lengths <, =and > Lc): combinations of (e) and (f).

In a number of situations, the analysis of the hybridization signals and of their distance, in the case where they would be aligned, should moreover provide additional information.

The example in diagram 1a (e) will illustrate this idea: in this case of an insertion, it is necessary to imagine that any segment which is not hybridized, but which is surrounded by two colinear hybridizations (of any size), is capable of representing an insertion: a histogram of these measurements will therefore be constructed; if an insertion really exists, it should therefore appear as a peak, in the same way as any hybridization.

This measurement will also serve in the case of deletions or of translocations, for example.

The technique disclosed above assumes that the hybridized combed genetic DNA is intact. Indeed, the reference situation, that of a healthy individual whose DNA corresponding to the clone used for the hybridization is not modified, is theoretically represented by a peak at the value of the length of the clone.

In practice, the DNA is subjected to hydromechanical stresses during its preparation, and also during the combing, which leads to numerous random breaks. These random breaks may occur within the target sequence for the probe, which will give rise, after combing, to a separation into several pieces of said sequence. During the hybridization with the probe, these segments will be hybridized, and after revealing, measured as fragments whose size is less than that of the target sequence.

These breaks will not necessarily affect all the target sequences in all the genomes used for the combing. Depending on the number of human genomes combed on the surface studied, and depending on the preparation conditions, the proportion of target sequences broken will remain reasonably small. In this case, the ideal histogram consisting of a single peak at the length of the probe will be replaced by a smaller peak accompanied by a distribution tail at lower lengths. Experience and basic practical considerations show that an optimum number of combed genomes per surface studied is at least approximately ten per combed surface under the experimental conditions described.

In the text which follows, simulations of break processes (following the preparation and the combing of the DNA), depending on two parameters, which make it possible to evaluate the influence, on the theoretical histogram, of the lengths of these phenomena, will be studied.

Two parameters appear to be important in the break phenomenon: the characteristic size and the break level.

The characteristic size defines approximately the size limit reached by molecules subjected to a large number of manipulations. One example of possible manipulation is pipetting: depending on the diameter of the cone of the pipette, the maximum size limit of the molecules will be larger or smaller. Another example of manipulation is the vortexing of the DNA solution.

The break level is thought to represent a model of the number of manipulations: for example, the higher the number of pipetting, the greater the risk of the molecules being broken.

A. Step Model

The easiest way of representing a model of the manipulations of DNA in solution consists in attributing a zero probability of a break to the fragments having a size less than the characteristic size $L_o$ and a probability of a break equal to 1 for the fragments having a size greater than $L_O$. The break in a fragment having a size L is made, in addition, randomly into any two fragments:

$L<L_o => P_o(L)=0$ $L>L_o => P_o(L)=1$

In order to introduce a break level into this model, a parameter sets the number of break processes to which a molecule and its successive fragments are subjected.

This model makes it possible to simulate the expected histograms during a hybridization of a probe of known length $L_c$ as a function of the parameters of the model. The conditions chosen are: probe hybridizing with a chromosome of 50 Mb, 200 combed genomes, $L_c$=50 kb.

A.1. Influence of the Characteristic Size on the Histogram

FIG. 4 represents, for various break levels (or steps), the shape of the theoretical histograms obtained for characteristic size values ($L_o$, $L_{break}$) of 1, 2, 4 or 8 times the size of the probe. It appears clearly that the closer the characteristic size to the size of the probe, the more the histogram becomes differentiated from the single peak described in part 2, the tail of the distribution at lengths shorter than the length $L_c$ of the probe becoming greater, until it practically causes the peak to disappear for the expected value $L_c$.

A.2. Influence of the Break Level on the Histogram

FIG. 5 presents, for different characteristic sizes, the variation of the theoretical histogram as a function of the break level, that is to say the number of random break steps (N time steps). It appears naturally that the peak at the expected length $L_c$ decreases when the break length increases.

In this model, however, the peak does not disappear completely, even when the break level increases indefinitely, since no break takes place when all the remaining fragments have a size less than $L_c$.

A.3. Advantage of the Model

The main advantage of the preceding model is to provide a rapid means for evaluating the probable shape of the histogram of the lengths of the probe fragments hybridized, so as to be able to interpret the results of the observations.

B. Gaussian Model

A slightly more realistic model consists in a similar model of successive break steps, but with a break law different from the "all-or-nothing" law of the step model. A simple way of "rounding off" this law is to replace the preceding probability by a Gaussian break law of probability:

$$P_G(L)=1-e^{-(L/Lo)^2}$$

B.1. Influence of the Characteristic Size on the Histogram

FIG. 6 represents, for various break levels, the shape of the theoretical histograms obtained for characteristic size values ($L_o$, $L_{break}$) of 1, 2, 4 or 8 times the size of the probe, which are identical to those used in the simulation carried out in the context of the step model. Likewise, the closer the characteristic size to the size of the probe, the more the histogram becomes differentiated from the single peak described in part 2, the tail of the distribution at lengths shorter than the length LC of the probe becoming greater, until it practically causes the peak to disappear for the expected value $L_c$.

B.2. Influence of the Break Level on the Histogram

FIG. 5 presents, for various characteristic sizes, the variation of the theoretical histogram as a function of the break level, that is to say the number of random break steps (N time steps). It appears naturally that the peak at the expected length $L_c$ decreases when the break level increases.

However, this model has a more realistic behavior than the preceding one since when the break level increases, the peak corresponding to $L_c$ decreases regardless of the value of the characteristic size, disappearing completely when the break level increases indefinitely.

B.3. Advantage of the Model

The Gaussian model being more realistic, it will be the one which we will use in the text which follows to simulate histograms of lengths of probe fragments hybridized.

C. Simulation of a Hybridization to a Break Point

To study the conditions for the applicability of our technique, we will present the simulation of three types of situations characteristic of the hybridization of a clone to a break point. We will take as example the case of a BAC (Bacterial Artificial Chromosome) of 125 kb covering a break point involved in a translocation (cf. for example diagram 2a (c1)).

Figure 8A:
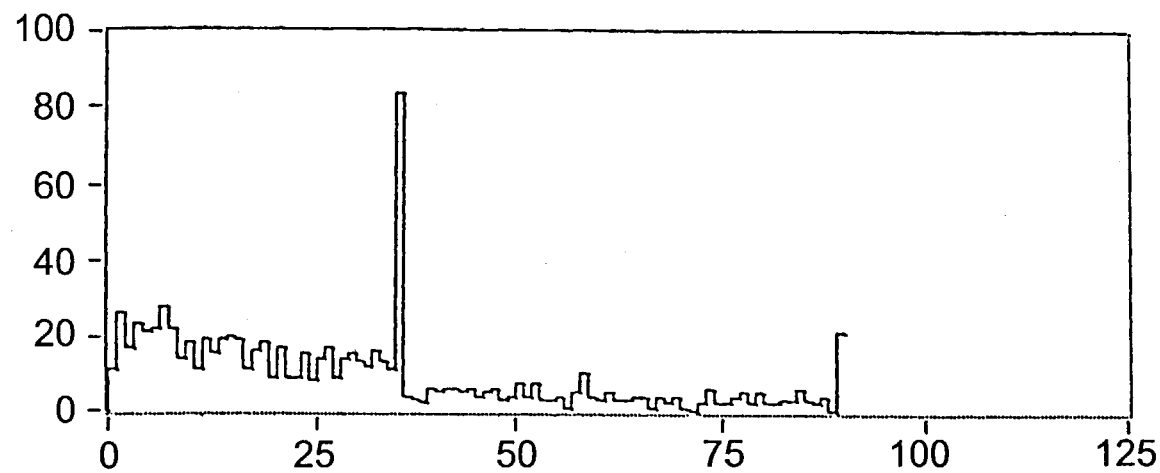
Figure 8A:
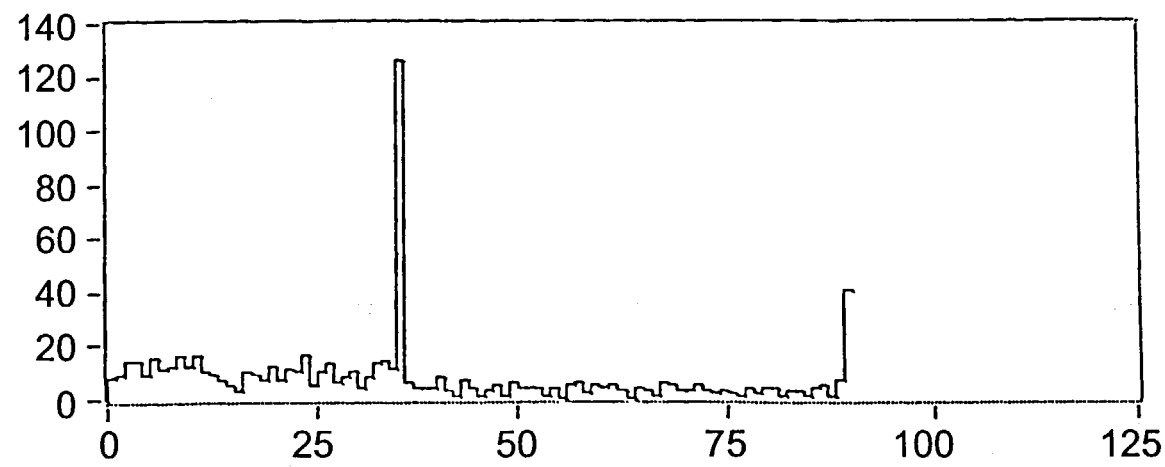
Figure 8B:
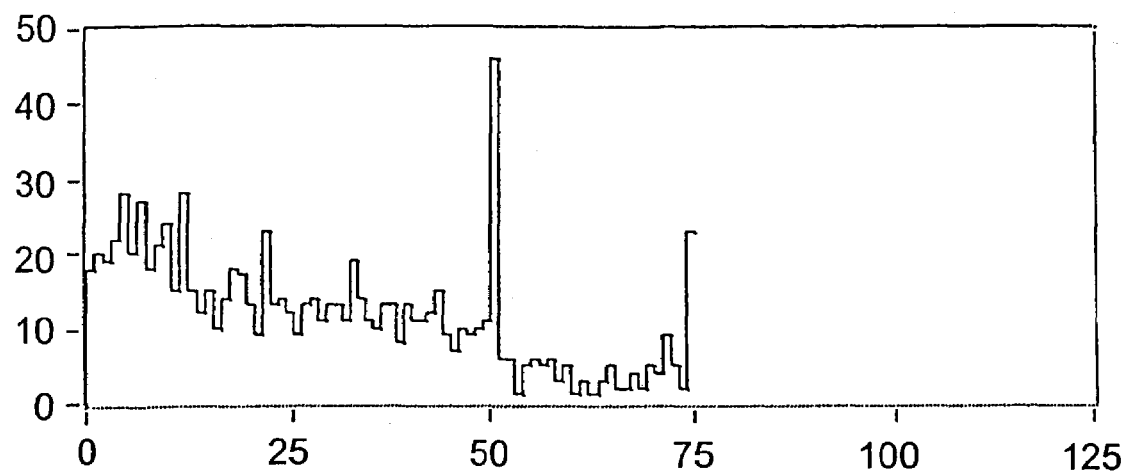
Figure 8B:
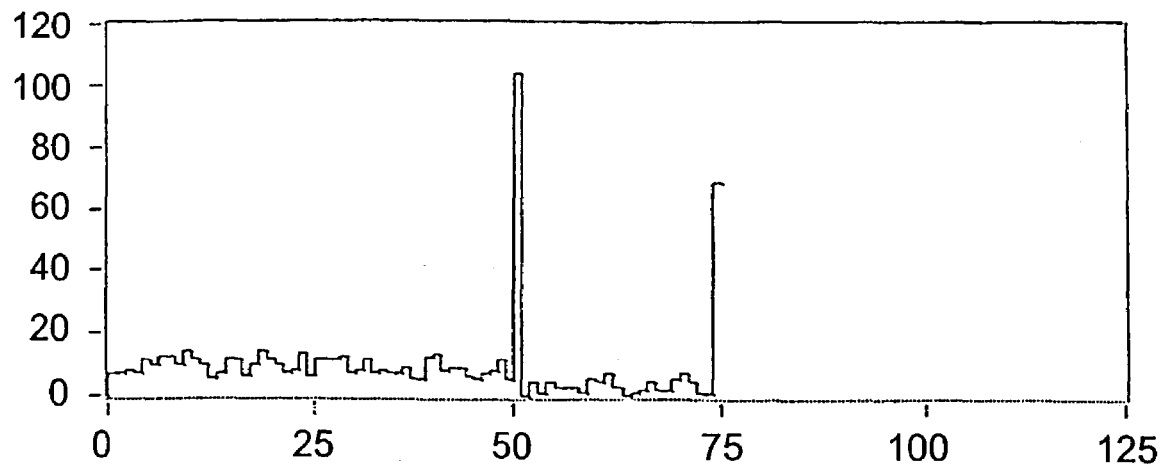
Figure 8C:
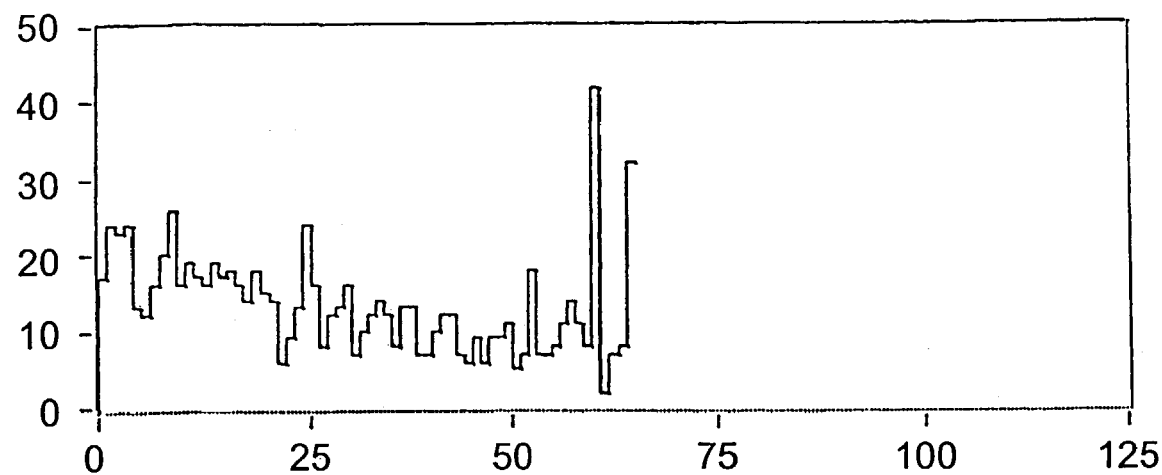
Figure 8C:
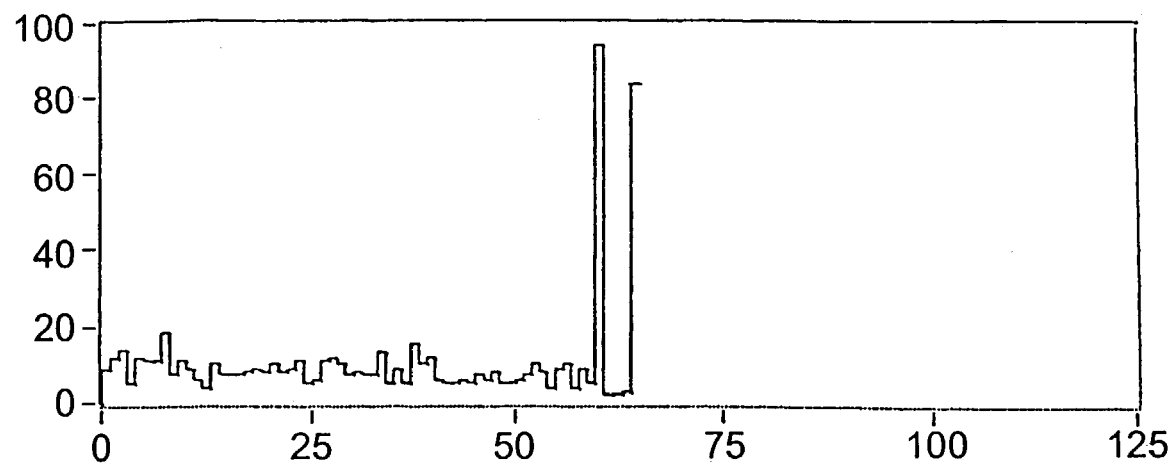
Figure 8D:
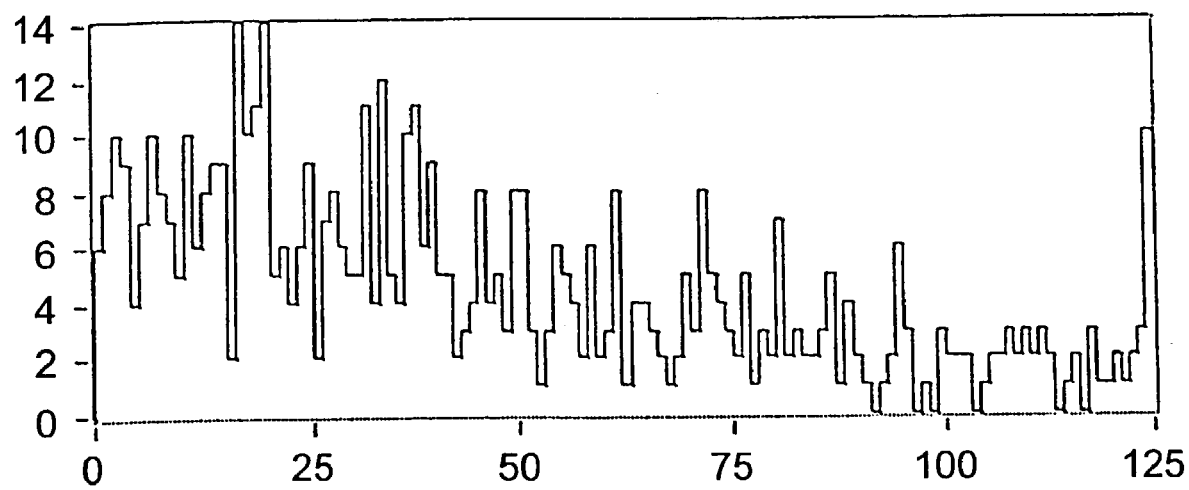
Figure 8D:
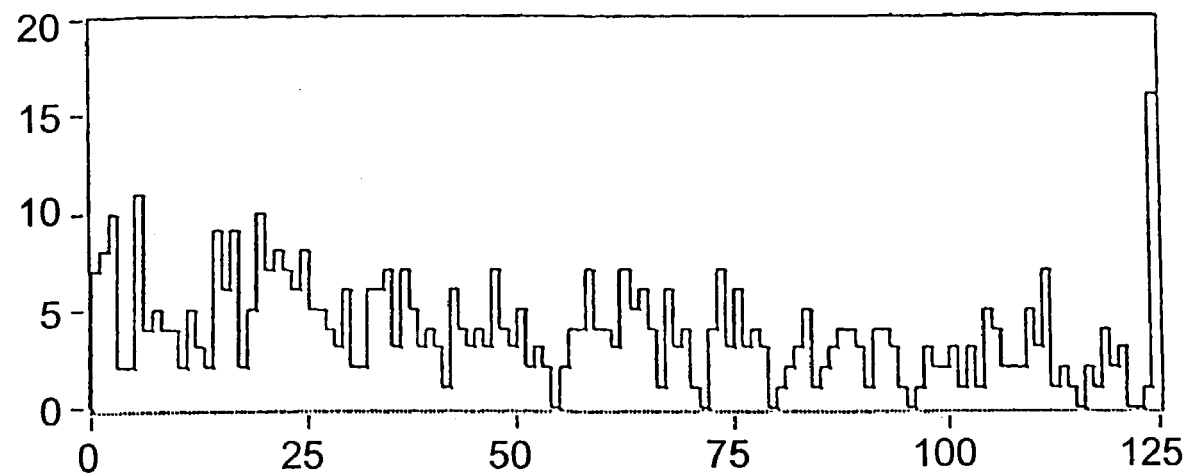

The simulations presented in FIG. 8d correspond to a situation where the clone is hybridized to a normal genomic DNA: under these conditions, most of the hybridizations have a length of $L_c$=125 kb, apart from the fragments broken because of the manipulations. We chose two values of the characteristic size $L_o$: $L_o$=100 ($<L_c$) and $L_c$=200 ($>L_c$). The break level is unique and equal to N=10.

These histograms show that it is possible to distinguish a peak at 125 kb in most cases, even when they are fairly unfavorable such as in the case $L_o$=100, N=10.

C.1. Fragments of 35 and 90 kb

FIG. 8a presents the results of the simulation of a histogram of the lengths of fragments hybridized in the case where the BAC of 125 kb hybridizes in two non-closely related portions of the genome, of very different sizes (35 and 90 kb), as in the case described in the diagram 2a (c1).

In the two cases ($L_o$=100, $L_o$=200), the two peaks at 35 and 90 kb are recognizable, even if the situation is considerably more favorable in the case where the characteristic size is considerably greater than the largest fragment.

It should be noted, moreover, that even in the case of a smaller sample, which would lead to a peak at 90 kb which is not very distinct, the peak at 35 kb would remain, indicating an abnormality relative to the normal size of the clone.

C.2. Fragments of 50 and 75 kb

FIG. 8b represents the result of simulations in the case of two fragments whose sizes are not very different from each other. Here again, the corresponding peaks are well defined and different from each other. In this case, it is possible to predict that with a smaller sample, it will remain possible to identify these two peaks.

C.3. Fragments of 60 and 65 kb

FIG. 8c represents the result of simulations in the case of two fragments of very similar sizes. In both cases, the peaks stand out clearly from the histogram of the small fragments, but there is the fear that the limited accuracy of the measurements blend them into only one.

Here again such information will however be sufficient to allow for the existence of a break point situated midway from the hybridized BAC.

C.4. Conclusions

The preceding simulations show that, under conditions avoiding excessively breaking the DNA before and during combing, it is possible to unambiguously distinguish between a control situation where the probe hybridizes to a normal human genome, and a situation where the probe hybridizes to a genome modified by the presence of a break point.

The heuristic parameters characterizing combing show that it is however preferable to have a characteristic size greater than or equal to the maximum hybridization length. The latter being unknown, a simple criterion is therefore a characteristic size of the order of or greater than the length of the clone used as probe.

To judge experimentally the achievement of this criterion, it therefore seems desirable to use, in addition to the probes intended for the search for an abnormality in the genome, a control probe of comparable size which hybridizes to a different portion of the genome. The corresponding histogram would thus make it possible to determine qualitatively the parameters for the model reflecting the experimental situation.

Figure 8E:
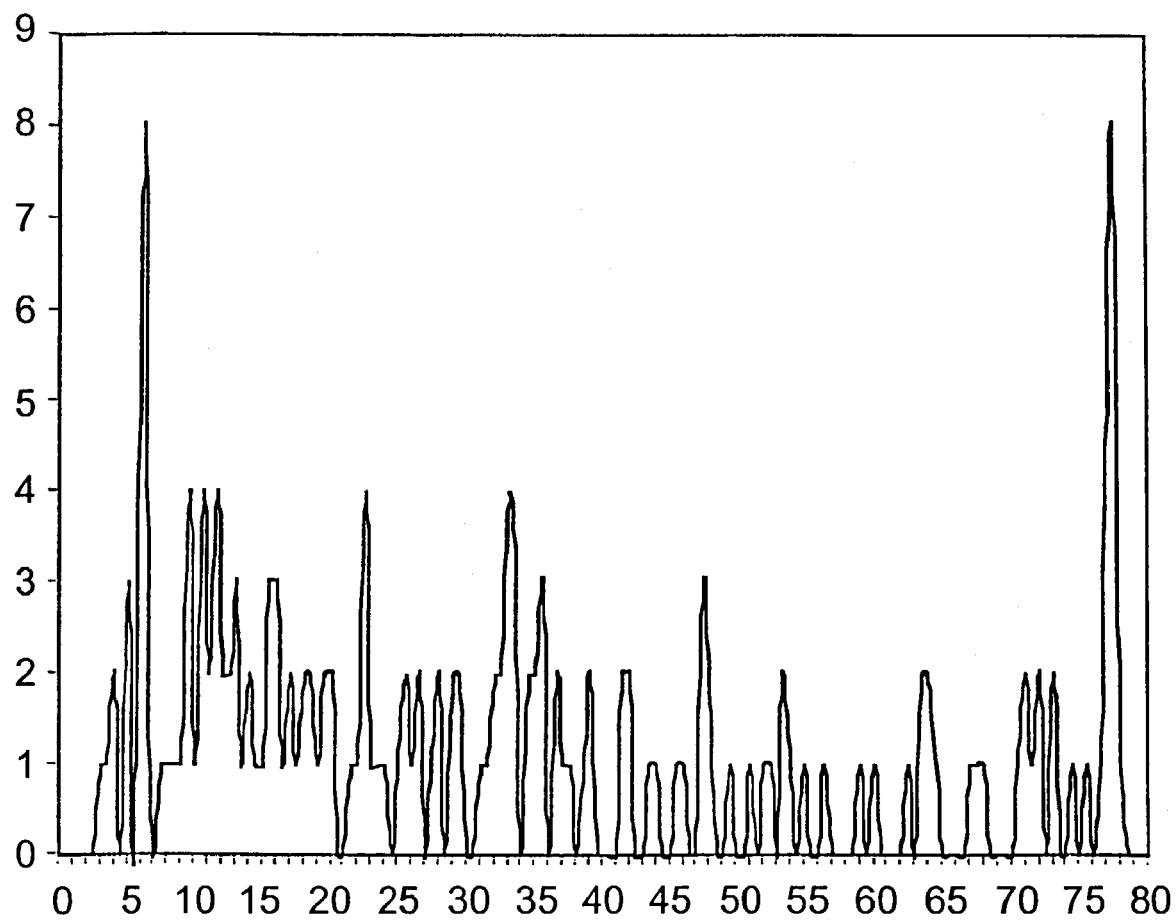

FIG. 8e illustrates an experimental implementation of the preceding example described in FIG. 8a. Human genomic DNA was combed according to the protocol described below. Five contiguous cosmid probes of chromosome 9 (280A6, 37A1, 149B8, 134A11, 99B4 belonging to the contig of the TSC1 gene) of about 155 kb in total were hybridized to this DNA and then revealed with fluorescent antibodies. A histogram of the hybridization lengths measured was plotted which is very similar to the histogram of FIG. 8d for $L_{break}$=100. It is noted, moreover, that the real histogram was obtained on an equivalent of less than 40 diploid genomes (simulations corresponding to 100 diploid genomes).

Surface Treatment

Slides of 22×22 mm are prepared and coated with silane using the method described in patent applications PCT/FR95/00164 and PCT/FR95/00165.

Preparation of the Cosmid Probes

The cosmid DNA is labeled by extension from a random primer with nucleotides modified with digoxygenin or which are biotinylated. For the probes labeled with biotin, the Bioprime™ DNA labeling "kit" (Gibco-BRL) containing random octameric primers and biotin-14-dCTP are used. For the labeling with digoxigenin, a different mixture of dNTPs is used which contains dCTP, DATP and dGTP (0.1 mM), dTTP (0.065 mM) and dig-11-dUTP (0.033 mM).

The size and the concentration of the labeled DNA fragments are confirmed by electrophoresis on a 0.6% agarose gel and by densitometry on bands. The labeling efficiency is evaluated using spots deposited on nylon membranes using serial dilutions of digoxigenin probes and of biotin probes. After incubation with an anti-dig alkaline phosphatase (AP) (Boehringer Mannheim) or streptavidin AP (Gibco-BRL), the spots are revealed with N BT (NitroBlue Tetrazolium) and BCIP (5-bromo-4-chloro-3-indolylphosphate) from Gibco-BRL. The positive spots are compared with the results obtained from control DNA samples labeled with dig or with biotin.

In order to limit the background noise, the strains are finally purified on Bio-Spin 6 columns (Biorad) by centrifugation for 5 min at 1500 g.

Solution of Yeast DNA

Yeast DNA containing YAC 774G4 (1600 kb) is prepared in 100 µl blocks of 0.8% LMP agarose (1 µg/block) using a protocol for preparing standard PFGE blocks. The blocks are stored in 0.5 M EDTA at 4° C. and rinsed with 15 ml TE buffer (10 mM Tris/1 mM EDTA, pH 8) for 2 hours before being used. Each block is stained with 3.3 µM YOYO-1 (Molecular Probes) in 100 µl $T_{40}E_2$ (40 mM Tris/2 mM EDTA, pH 8) for 1 hour at room temperature (RT). The agarose is then melted for 45 minutes at 68° C. and digested for 2 hours at 40° C. using 2 U of β-agarase I in a 1×NEB agarase buffer (Biolabs) per block.

The dilution of the DNA (0.25 µg/ml) in 50 mM MES (pH 5.5) is carried out with great care in order to avoid breaking the DNA strands. The solution is then poured into a 4 ml Teflon™ reservoir allowing the introduction of 3 silanized 22×22 mm slides for combing. The DNA solution may also be stored at 4° C. for several days.

Molecular Combing

The silanized slides are soaked in the Teflon™ reservoir containing a solution of total yeast DNA (0.25 g/ml in 50 mM MES, pH 5.5), incubated at RT and extracted from the reservoir after 10 minutes of incubation using a simple mechanical device. During the incubation, the DNA molecules become anchored on the surface by their ends. By extracting the surface from the reservoir, this has the same effect as the evaporation provided for in the "drop method", the meniscus moves relative to the surface and exerts a constant pulling force on the molecules remaining in the reservoir.

The surfaces covered with the combed DNA are then examined with an epifluorescence microscope so as to check the combing characteristics. A recording of the representative fields of view for each slide is carried out for the post-hybridization check.

The surfaces are then bonded to microscope slides (cyanocrylate) and heated overnight at 60° C. They can be stored for several months if they are protected from moisture at −20° C. or at room temperature. The surfaces are then dehydrated before denaturation using a bath containing increasing concentrations of ethanol (70%, 90%, 100%).

Denaturation and Hybridization

The surfaces are denatured in 70% deionized formamide/30% 2×SSC, pH 7.0) for 4 minutes at 70_C. and immediately immersed for 5 minutes in a cold ethanol bath (0° C.) at increasing concentrations (70%, 90%, 100%). The surfaces are then allowed to dry.

50 ng of biotin-labeled probes and 50 ng of digoxygenin-labeled probes are then mixed with 3 µg of human DNA Cot1 and 10 µg of herring sperm DNA in 10 µl of hybridization buffer (50% deionized formamide/10% dextran sulfate/2×SSC/1% Tween 20, pH 7). The probes are denatured for 5 minutes at 80° C. and immediately refrigerated. at 0° C.

10 µl of the probe solution are added per 22×22 mm combed slide and then covered with an untreated slide and sealed with a rubber-cement type polymer marketed by Sanford, USA. The hybridization is carried out overnight at 37° C. in a humid chamber (HC).

Revealing with Fluorescent Probes

After hybridization, the slides are washed for 5 minutes at RT in 3 baths (50% deionized formamide/2×SSC, pH 7) and for 5 minutes to 5' at RT in 3 baths of 2×SSC. The slides are incubated for 30 minutes at 37° C. (HC) with 50 µl per slide of a blocking solution (1.5% −w/v) of reagent (Boehringer Mannheim) in 4×SSC/0.05% Tween 20, pH 7.2).

The detections of the biotin- and digoxigenin-labeled probes are carried out simultaneously using the same protocol for each detection layer, each antibody layer being incubated for 30 minutes at 37° C., the slides being washed after each layer (3 times 5 minutes at RT in 4×SSC/0.05% Tween 20).

For the biotin-labeled probes, the following layers are used (50 µl of hybridization buffer per slide) : (1) 40 mg/ml of Avidin-Texas Red (Vector). (2) 5 mg/ml of goat anti-biotinilated avidin (Vector). (3) 40 mg/ml of Avidin-Texas Red (Vector).

For the digoxigenin-labeled probes: (1) 34 mg/ml of a mouse anti-dig conjugate with FITC (Jackson). (2) 28 mg/ml of donkey anti-mouse-FITC (Jackson). (3) 30 mg/ml of mouse anti-rabbit-FITC (Jackson).

After detection, the slides are rapidly rinsed in 1×PBS and mounted with a reagent (Vectashield, Vector) before examination. The slides may be kept for months at 4° C. in the dark.

EXAMPLE 1

In the case of the combing of human genomic DNA, simultaneous hybridizations of two cosmids separated by a gap of several tens of kb (180F1 and 50D9) are carried out: it was possible to measure about 80 coupled signals (cosmid 1–gap–cosmid 2) on a single 22×22 mm coverslip, corresponding to a total distance of about 120 kb (see Example 5).

This result makes it possible to ensure that it is possible to observe about 100 hybridizations of a whole BAC on a normal human genome. This experimental situation is to be compared with the theoretical situations envisaged in FIG. 8: the histograms 8d indeed show that for 100 diploid genomes (therefore 200 occurrences of a cloned sequence), and with particular parameters, about 10 intact hybridization signals of a BAC of 125 kb (case $L_o$=100 kb), or 16 intact hybridization signals (case $L_o$=200 kb) are expected. In other words, the theoretical parameters used in the simulations are a lot more pessimistic than the experimental conditions which it is currently possible to produce.

This theoretical and experimental analysis as a whole therefore allows a first validation of the present invention.

In addition to the search for break points with the aid of BACs (or other probes of equivalent or smaller size) which is mentioned above, it is also possible to envisage using YACs (available for the entire human genome, and for other genomes). Simulations similar to those presented above show that it is possible to envisage detecting the hybridization of a YAC of 1600 kb in two distinct fragments of 400 and 1200 kb (for example) on the basis of 100 combed genomes under conditions corresponding to $L_o$=600, N=10 in the Gaussian model.

However, in contrast to the observations of BACS or of probes of a similar or a smaller size, which may be carried out without difficulty with the aid of an epifluorescence microscope equipped with a ×100 or ×63 lens and a camera (maximum size of a field of view; respectively 123 µm and 195 µm approximately), the measurement of fragments of several hundreds of kb requires the use of lenses with a lower magnification, for which problems of detectability of the signals may possibly exist:

×40: field of view of maximum size 307 µm approximately.
×20: field of view of maximum size 614 µm approximately.

The advantage of using such large probes is obviously to reduce the number of hybridizations necessary in order to find a clone of interest.

EXAMPLE 2

Assay of the λ Phage DNA in the Genome of *E. Coli*

Genomic DNA of *E. Coli* (1c=4.7 Mb) containing one copy of the λ phage genome (line 5243, lt=49 kb) was combed on silanized surfaces after having been counter-stained with a fluorescent molecule (YOYO-1).

The total length of combed DNA per field of view was estimated from 30 to 50 fields of view uniformly distributed over the whole of each surface.

Biotin-dUTP labeled λ phage DNA was then hybridized and revealed with the aid of a system of antibodies coupled to FITC (green). The total length of hybridized DNA per field of view was estimated from 100 fields of view uniformly distributed over the whole of each surface.

The results of 4 experiments are represented in the table below in which $$Nb\ E.\ coli = \frac{Lc}{lc}\ \text{and}\ Nb = \frac{LT}{lt}$$

|  | Nb *E. Coli* | Nb λ | R = λ/*E. Coli* | ΔR |
|---|---|---|---|---|
| 43_4 | 0.19 | 0.19 | 1.0 | 0.6 |
| 43_6 | 0.25 | 0.22 | 0.9 | 0.5 |
| 43_7 | 0.31 | 0.26 | 0.8 | 0.4 |
| 43_8 | 0.20 | 0.24 | 1.2 | 0.7 |
| 43_9 | 0.26 | 0.39 | 1.5 | 0.8 |
| 43_13 | 0.57 | 0.74 | 1.3 | 0.4 |
| 43_14 | 0.61 | 0.56 | 0.9 | 0.3 |

These results showed, except for slide 43_9, a ratio which is reasonably close to the expected value of 1. However, the principle used, consisting in measuring all the signals before hybridization, is not very practicable for larger genomes (the error ΔR is mainly due here to the small number of *E. Coli* genomes measured, of the order of 6 to 24).

EXAMPLE 3

Assay of the Number of Amplicons in the Genome of Hamster Cells

The feasibility study was extended to mammalian genomic DNA. The system chosen is the DNA of 2 hamster lung fibroplast lines (lines 618 and GMA32) containing respectively 1 and 2 copies of the target gene AMP1 per haploid genome.

Genomic DNA of cells which is provided in solution was combed on silanized surfaces, with an estimated density of 100 diploid genomes per 22×22 mm surface.

A cosmid probe (D3S1, ~40 kb)) specific for the target gene region was labeled with dig-dUTP. Another cosmid probe (565.5A1, ~40 kb), specific for a region situated at about 1 Mb from the target gene was used as control, and labeled with biotin-dUTP.

The probes were hybridized to previously denatured combed genomic DNA, and were revealed in red (biotinilated probes) and green (digoxygenated probes) in one of the cases, and with reversed colors in the other. The hydridization signals for each color were measured on a number of fields of view which is representative of the surface.

In the case of line A32, the total size obtained for probe D3S1 (1400 µm approximately) represents 70 copies of the gene. The size obtained on the same fields of view for the control probe (1180 µm approximately) represents, for its part, 60 haploid genomes. This measurement therefore gives a target/control ratio of 1.2±0.3 which is compatible with the presence of one copy of the gene per haploid genome.

These experiments therefore show the feasibility of the gene assay using solely the hybridization signals of target and control probes, as long as a sufficient number of signals can be observed.

EXAMPLE 4

Mapping in Pairs of 6 Cosmids on a YAC of 1600 bp Contained in Yeast Genomic DNA YAC 774G4 contains a human genomic DNA clone of chromosome 15 containing the calpain gene (CANP3), whose mutation is responsible for a girdle dystrophy (LGMD 2A). In collaboration with J. Beckman's group at Généthon (Evry), we have combed yeast genomic DNA contained in blocks of Low Melting agarose (1 block, 1 μg of DNA per block) on silanized surfaces.

The six cosmids were hybridized in pairs and the measurement of their respective size and distance was carried out by producing histograms of the sizes and distances. The mean and standard deviation for the main peak of each histogram were extracted therefrom with the aid of specific software. The standard deviation of the measurements is found to be of the order of 2 to 4 kb (FIG. 11).

EXAMPLE 5

Mapping of Pairs of Cosmids on Human Genomic DNA 4 cosmids belonging to 3 adjacent contigs separated by gaps were used in 2 series of hybridizations, carried out in collaboration with S. Povey's group at MRC (London). The contigs cover the region of the TSC 1 gene involved in one of the forms of tuberous sclerosis (chromosome 9). The cosmid probes were prepared according to the protocol above.

The genomic DNA used was extracted from cell cultures and placed in a block of Low Melting agarose at the rate of $10^6$ cells per block. 3 blocks treated according to the preceding protocol (reservoir of 4 ml, use of final molarity of MES pH 5.5 of 150 mM), were used for the combing of the genomic DNA.

The cosmids were hybridized in pairs on similar slides, a total of several tens of double signals (red/green aligned) per slide being observed on average. The same measurement protocol as above was observed, giving rise to final values having the same accuracy as in the preceding experiment.

FIG. 12 presents a few typical images which allowed the measurement of the sizes of the 2 gaps studied.

EXAMPLE 6

Mapping of Restriction Segments

This mapping technique is naturally applicable to any other type of combed DNA or subclone. A possible extension of the technique would consist, for example, in no longer mapping subclones of a clone, but directly mapping restriction fragments of the combed DNA (for example a clone of the BAC type).

This would avoid the production of intermediate subclones before sequencing, the physical map of the restriction fragments being obtained with sufficient accuracy to allow a reconstitution of the final sequence. The applicability of this technique rests on a good separation of the restriction bands, and adequate size (>10 kb) of the main fragments, as well as on the subsequent subcloning of the DNA of these bands (subcloning into small-sized vectors, after additional enzymatic restriction, for sequencing).

The invention claimed is:

1. A method of determining the position of $p''$ cloned nucleotide sequences within a genome, comprising:
   (a) providing a surface on which genomic DNA has been aligned using a molecular combing technique with the aid of a receding meniscus;
   (b) contacting the aligned genomic DNA with labeled probes, wherein the labeled probes comprise nucleotide sequences that are complementary to the cloned nucleotide sequences;
   (c) detecting hybridization between the labeled probes and the genomic DNA; and
   (d) determining the position of the labeled probes, the distance between the labeled probes, or the size of the labeled probes, and deducing therefrom the position of the $p''$ cloned nucleotide sequences,
   wherein parts b) and c) are repeated "n" times by modifying the color, the labeling, or the mode of revealing the probes, so that if the number of colors, labelings, or modes of revealing equals "p", it is possible to position $p''$ cloned nucleotide sequences after "n" hybridizations,
   wherein the position of the labeled probes, the distance between the labeled probes, or the size of the labeled probes is converted into a histogram.

2. The method according to claim 1, wherein the label is fluorescent or radioactive.

3. The method according to claim 1, wherein the label is fluorescent.

4. The method of claim 1, wherein the probes are labeled with modified nucleotides.

5. The method according to claim 4, wherein the modified nucleotides are modified with biotin, digoxigenin (DIG), or other haptens.

6. The method of claim 1, wherein the probes are nucleotide probes in which some atoms have been replaced.

7. The method of claim 1, wherein the surface comprises at least 10 copies of the genomic DNA.

8. The method of claim 1, wherein the surface further comprises a calibrating DNA, for calibrating a measurement.

9. The method of claim 1, wherein the genomic DNA is obtained from a sample of biological fluid or from a tissue of biological origin.

10. The method of claim 9, wherein the genomic DNA is obtained from a biological material containing at least 80% of genetic material of fetal origin.

* * * * *

UNITED STATES PATENT AND TRADEMARK OFFICE
CERTIFICATE OF CORRECTION

| | | |
|---|---|---|
| PATENT NO. | : 7,368,234 B2 | Page 1 of 1 |
| APPLICATION NO. | : 10/386354 | |
| DATED | : May 6, 2008 | |
| INVENTOR(S) | : Bensimon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 397 days.

Signed and Sealed this
Eighth Day of February, 2011

David J. Kappos
*Director of the United States Patent and Trademark Office*